(12) United States Patent
Iding et al.

(10) Patent No.: US 7,151,111 B2
(45) Date of Patent: *Dec. 19, 2006

(54) 4-PYRROLIDINO-PHENYL-BENZYL ETHER DERIVATIVES

(75) Inventors: Hans Iding, Rheinfelden (DE); Synese Jolidon, Blauen (CH); Daniela Krummenacher, Rheinfelden (CH); Rosa Maria Rodriguez-Sarmiento, Basel (CH); Andrew William Thomas, Birsfelden (CH); Beat Wirz, Reinach (CH); Wolfgang Wostl, Grenzach-Wyhlen (DE); Rene Wyler, Zurich (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 361 days.

This patent is subject to a terminal disclaimer.

(21) Appl. No.: 10/667,087

(22) Filed: Sep. 18, 2003

(65) Prior Publication Data

US 2004/0116707 A1    Jun. 17, 2004

(30) Foreign Application Priority Data

Sep. 20, 2002  (EP) .................................. 02021319

(51) Int. Cl.
*A61K 31/44* (2006.01)
*A61K 31/40* (2006.01)
*C07D 401/06* (2006.01)
*C07D 207/06* (2006.01)

(52) U.S. Cl. ...................... 514/343; 514/423; 514/424; 546/278.4; 548/537; 548/550

(58) Field of Classification Search ................ 514/423, 514/424, 343; 546/278.4; 548/537, 550
See application file for complete search history.

(56) References Cited

U.S. PATENT DOCUMENTS 4,287,351 A    9/1981  Bourgery et al.

2004/0097578 A1*  5/2004  Jolidon et al. ............... 514/424
2004/0106650 A1*  6/2004  Iding et al. .................. 514/343

FOREIGN PATENT DOCUMENTS

| EP | 0 393 607 | 10/1990 |
|---|---|---|
| FR | 2 500 831 | 9/1982 |
| WO | WO 96/40095 | 12/1996 |
| WO | WO 97/33572 | 9/1997 |
| WO | WO 01/34172 | 5/2001 |

OTHER PUBLICATIONS

Bach, A. W. J., et al. Proc. Natl. Acad. Sci. USA 85:4934-4938 (1988).
Cesura, A. M., & Pletscher, A., Prog. Drug Research 38:171-297 (1992).
Fowler, C.J., et al. J. Neural. Transm. 49:1-20 (1980).
Benedetti, M. S., et al. Biochem. Pharmacol. 38:555-561 (1989).
Saura, J., et al. Neuroscience 70:755-774 (1996).
Bentué-Ferrer, D., et al. CNS Drugs 6(3): 217-236 (1996).
Gardner, D. M., et al. J. Clin. Psychiatry 57(3):99-104 (1996).
Lam, P. Y. S., et al. Tetrahedron Lett. 43:3091-3094 (2002).
Lam, P. Y. S., et al. Synlett 5:674-676 (2000).
Chan, D. M. T., et al. Tetrahedron Lett. 39:2933-2936 (1998).
Wolfe, J. P., et al. J. Amer. Chem. Soc. 118:7215-7216 (1996).
Zhou, M., & Panchuk-Voloshina, N., Analytical Biochemistry 253:169-174 (1997).

* cited by examiner

*Primary Examiner*—Golam M. M. Shameem
*Assistant Examiner*—Ebenezer Sackey
(74) *Attorney, Agent, or Firm*—George W. Johnston; Patricia S. Rocha-Tramaloni; Kimberly J. Prior

(57) ABSTRACT

The invention relates to racemic or enantiomerically pure 4-pyrrolidino derivatives, processes for their preparation, pharmaceutical compositions comprising said derivatives, and their use in the prevention and treatment of a disease which is mediated by a monoamine oxidase B inhibitor, in particular Alzheimer's disease and senile dementia.

51 Claims, No Drawings

4-PYRROLIDINO-PHENYL-BENZYL ETHER DERIVATIVES

FIELD OF THE INVENTION

The present invention relates to new 4-pyrrolidino derivatives, to processes and intermediates for their preparation, and to pharmaceutical compositions containing them. These compounds are selective monoamine oxidase B inhibitors and, therefore, are useful for treating or preventing diseases mediated by monoamine oxidase B.

BACKGROUND OF THE INVENTION

Monoamine oxidase (MAO, EC 1.4.3.4) is a flavin-containing enzyme responsible for the oxidative deamination of endogenous monoamine neurotransmitters such as dopamine, serotonin, adrenaline, or noradrenaline, and trace amines, e.g. phenylethyl-amine, as well as a number of amine xenobiotics. The enzyme exists in two forms, MAO-A and MAO-B, encoded by different genes [Bach et al., Proc. Natl. Acad. Sci. USA 85:4934–4938 (1988)] and differing in tissue distribution, structure and substrate specificity. MAO-A has higher affinity for serotonin, octopamine, adrenaline, and noradrenaline; whereas the natural substrates for MAO-B are phenylethylamine and tyramine. Dopamine is thought to be oxidised by both isoforms. MAO-B is widely distributed in several organs including brain [Cesura and Pletscher, Prog. Drug Research 38:171–297 (1992)]. Brain MAO-B activity appears to increase with age. This increase has been attributed to the gliosis associated with aging [Fowler et al., J. Neural. Transm. 49:1–20 (1980)]. Additionally, MAO-B activity is significantly higher in the brains of patients with Alzheimer's disease [Dostert et al., Biochem. Pharmacol. 38:555–561 (1989)] and it has been found to be highly expressed in astrocytes around senile plaques [Saura et al., Neuroscience 70:755–774 (1994)]. In this context, since oxidative deamination of primary monoamines by MAO produces $NH_3$, aldehydes and $H_2O_2$, agents with established or potential toxicity, it is suggested that there is a rationale for the use of selective MAO-B inhibitors for the treatment of dementia and Parkinson's disease. Inhibition of MAO-B causes a reduction in the enzymatic inactivation of dopamine and thus prolongation of the availability of the neurotransmitter in dopaminergic neurons. The degeneration processes associated with age and Alzheimer's and Parkinson's diseases may also be attributed to oxidative stress due to increased MAO activity and consequent increased formation of $H_2O_2$ by MAO-B. Therefore, MAO-B inhibitors may act by both reducing the formation of oxygen radicals and elevating the levels of monoamines in the brain.

Given the implication of MAO-B in the neurological disorders mentioned above, there is considerable interest to obtain potent and selective inhibitors that would permit control over this enzymatic activity. The pharmacology of some known MAO-B inhibitors is for example discussed by Bentué-Ferrer et al. [CNS Drugs 6:217–236 (1996)]. Whereas a major limitation of irreversible and non-selective MAO inhibitor activity is the need to observe dietary precautions due to the risk of inducing a hypertensive crisis when dietary tyramine is ingested, as well as the potential for interactions with other medications [Gardner et al., J. Clin. Psychiatry 57:99–104 (1996)], these adverse events are of less concern with reversible and selective MAO inhibitors, in particular of MAO-B. Thus, there is a need for MAO-B inhibitors with a high selectivity and without the adverse side-effects typical of irreversible MAO inhibitors with low selectivity for the enzyme.

SUMMARY OF THE INVENTION

The invention relates to racemic or enantiomerically pure 4-pyrrolidino derivatives, processes for their preparation, pharmaceutical compositions comprising said derivatives, and their use in the prevention and treatment of illness. More particularly, the present invention relates to compounds of the formula I

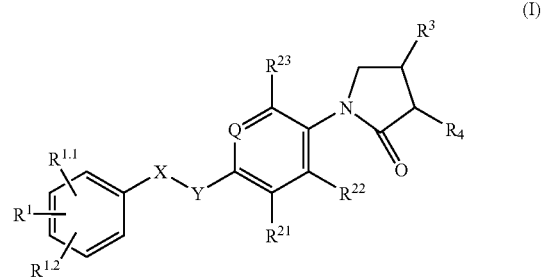

wherein Q is =N— or =C($R^{24}$)—; X—Y is —$CH_2$—$CH_2$—, —CH=CH— or —$CH_2$—O—; and $R^1$, $R^{1.1}$, $R^{1.2}$, $R^3$, $R^4$, $R^6$, $R^{21}$, $R^{22}$, $R^{23}$ and $R^{24}$ are as defined herein. The invention includes individual isomers of the compounds herein as well as racemic and non-racemic mixtures thereof.

It has been found that the compounds of general formula I and I* as well as individual isomers, racemic or non-racemic mixtures thereof (hereinafter: Active Compounds) are selective monoamine oxidase B inhibitors. Therefore, the invention relates to pharmaceutical compositions and methods for treating diseases mediated by MAO-B inhibitors, for example, Alzheimer's disease and senile dementia.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

The term "individual isomers, racemic or non-racemic mixtures thereof" denotes E- and Z-isomers, mixtures thereof as well as individual configurational isomers and mixtures thereof.

The term "($C_1$–$C_6$)-alkyl" used in the present application denotes straight-chain or branched saturated hydrocarbon residues with 1 to 6 carbon atoms, such as methyl, ethyl, n-propyl, i-propyl, n-butyl, sec-butyl, t-butyl, and the like, preferably with 1 to 3 carbon atoms. Accordingly, the term "($C_1$–$C_3$)-alkyl" means a straight-chain or branched saturated hydrocarbon residue with 1 to 3 carbon atoms.

"($C_1$–$C_6$)-Alkoxy" means the residue —O—R, wherein R is a lower alkyl residue as defined herein. Examples of alkoxy radicals include, but are not limited to, methoxy, ethoxy, iso-propoxy, and the like.

The term "halogen" denotes fluorine, chlorine, bromine and iodine.

"Halogen-($C_1$–$C_6$)-alkyl" or "halogen-($C_1$–$C_6$)-alkoxy" means the lower alkyl residue or lower alkoxy residue, respectively, as defined herein substituted in any position with one or more halogen atoms as defined herein. Examples of halogenalkyl residues include, but are not limited to, 1,2-difluoropropyl, 1,2-dichloropropyl, trifluoromethyl, 2,2,2-trifluoroethyl, 2,2,2-trichloroethyl, and 3,3,3-trifluoropropyl, and the like. "Halogenalkoxy" includes trifluoromethyloxy.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salts" of a compound means salts that are pharmaceutically acceptable, which are generally safe, non-toxic, and neither biologically nor otherwise undesirable, and that possess the desired pharmacological activity of the parent compound. These salts are derived from an inorganic or organic acid or base. If possible, compounds of formula I may be converted into pharmaceutically acceptable salts. It should be understood that pharmaceutically acceptable salts are included in the present invention.

It should be understood that all references to pharmaceutically acceptable salts include solvent addition forms (solvates) or crystal forms (polymorphs) of the same acid addition salt.

"Therapeutically effective amount" means an amount that is effective to prevent, alleviate or ameliorate symptoms of disease or prolong the survival of the subject being treated.

The invention relates to racemic or enantiomerically pure 4-pyrrolidino derivatives, processes for their preparation, pharmaceutical compositions comprising said derivatives, and their use in the prevention and treatment of illness.

More particularly, the present invention relates to compounds of the formula I

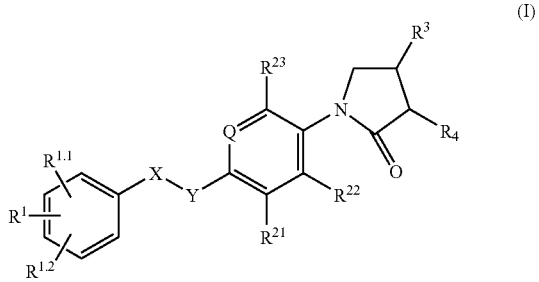

wherein
Q is =N— or =C($R^{24}$)—;
X—Y is —$CH_2$—$CH_2$—, —CH=CH— or —$CH_2$—O—;
$R^1$, $R^{1.1}$ and $R^{1.2}$ independently from each other are selected from the group consisting of hydrogen, halogen, halogen-($C_1$–$C_6$)-alkyl, cyano, ($C_1$–$C_6$)-alkoxy or halogen-($C_1$–$C_6$)-alkoxy;
$R^{21}$, $R^{22}$ and $R^{23}$ independently from each other are selected from the group consisting of hydrogen and halogen;
$R^{24}$ is hydrogen, halogen or methyl;
$R^3$ is —$NHR^6$;
$R^4$ is hydrogen; and
$R^6$ is —C(O)H, —C(O)—($C_1$–$C_3$)-alkyl, C(O)-halogen-($C_1$–$C_3$)alkyl, —C(O)O($C_1$–$C_3$)-alkyl, —C(O)$NH_2$ or —$SO_2$—($C_1$–$C_3$)-alkyl;

as well as individual isomers, racemic or non-racemic mixtures thereof.

Even more particularly, the present invention relates to compounds of the formula I*

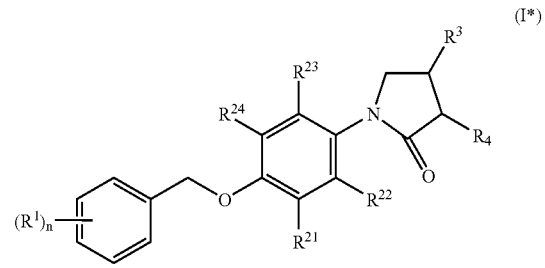

wherein
$R^1$ is halogen, halogen-($C_1$–$C_6$)-alkyl, cyano, ($C_1$–$C_6$)-alkoxy or halogen-($C_1$–$C_6$)-alkoxy;
$R^{21}$, $R^{22}$, $R^{23}$ and $R^{24}$ independently from each other are selected from the group consisting of hydrogen and halogen;
$R^3$ is —$NHR^6$;
$R^4$ is hydrogen;
$R^6$ is —CO—($C_1$–$C_3$)-alkyl or —$SO_2$—($C_1$–$C_3$)-alkyl; and
n is 0, 1, 2 or 3;

as well as individual isomers, racemic or non-racemic mixtures thereof.

In one embodiment the invention provides compounds of formula I*, wherein $R^3$ is —$NHR^6$, $R^6$ is —CO—($C_1$–$C_6$)-alkyl or —$SO_2$—($C_1$–$C_6$)-alkyl, and $R^4$ is hydrogen. An example for such a compound is (RS)—N—{1-[4-(3-fluorobenzyloxy)-phenyl]-5-oxo-pyrrolidin-3-yl}-acetamide.

Compounds of formula I* may be substituted by n $R^1$ selected from the group consisting of halogen, halogen-($C_1$–$C_6$)-alkyl, cyano, ($C_1$–$C_6$)-alkoxy or halogen-($C_1$–$C_6$)-alkoxy, wherein n denotes an integer selected from 0, 1, 2 and 3. Preferably n is 1 or 2.

Preferred compounds of formula I* are those, wherein $R^1$ is halogen or halogen-($C_1$–$C_6$)-alkyl. Especially preferred are those compounds of formula I*, wherein $R^1$ is fluorine, chlorine or trifluoromethyl. In still another aspect the present invention provides compounds of formula I* wherein n is zero or 1. In yet another aspect the present invention provides compounds of formula I* wherein n is 1. Where the compounds are substituted by two or three $R^1$, each $R^1$ can be the same or different.

In one embodiment the invention provides compounds of formula I wherein Q is =C($R^{24}$)—, wherein $R^{24}$ is hydrogen, halogen or methyl. In another embodiment the invention provides compounds of formula I wherein Q is =CH—, =CF— or =C($CH_3$)—. In still another embodiment the invention provides compounds of formula I wherein Q is =N—.

In one embodiment the invention provides compounds of formula I wherein —X—Y— is —$CH_2$—O—. In another embodiment the invention provides compounds of formula I wherein —X—Y— is —$CH_2$—$CH_2$— or —CH=CH—.

In one embodiment the invention provides compounds of formula I wherein $R^1$, $R^{1.1}$ and $R^{1.2}$ independently from each other are selected from the group consisting of hydrogen, halogen, methyl, halogenmethyl, cyano, methoxy or halogen-methoxy. In another embodiment the present invention provides compounds of formula I wherein $R^1$, $R^{1.1}$ and $R^{1.2}$ are halogen, e.g. fluoro, e.g. 2,4,6-trifluoro, 2,4,5-trifluoro, 2,3,6-trifluoro, 2,3,4-trifluoro or 3,4,5-trifluoro. In still another embodiment the present invention provides compounds of formula I wherein $R^{1.2}$ is hydrogen and $R^1$ and $R^{1.1}$ independently from each other are selected from the group consisting of hydrogen, halogen, $(C_1-C_6)$-alkyl, halogen-$(C_1-C_6)$-alkyl, cyano, $(C_1-C_6)$-alkoxy or halogen-$(C_1-C_6)$-alkyl. In still another embodiment the present invention provides compounds of formula I wherein $R^{1.2}$ is hydrogen and $R^1$ and $R^{1.1}$ independently from each other are selected from the group consisting of halogen and $(C_1-C_6)$-alkyl. In still another embodiment the present invention provides compounds of formula I wherein $R^{1.2}$ is hydrogen, $R^{1.1}$ is halogen and $R^1$ is halogen or $(C_1-C_6)$-alkyl. In still another embodiment the present invention provides compounds of formula I wherein $R^{1.1}$ and $R^{1.2}$ are hydrogen and $R^1$ is halogen, $(C_1-C_6)$-alkyl, halogen-$(C_1-C_6)$-alkyl, cyano, $(C_1-C_6)$-alkoxy or halogen-$(C_1-C_6)$-alkoxy. In still another embodiment the present invention provides compounds of formula I wherein $R^{1.1}$ and $R^{1.2}$ are hydrogen and $R^1$ is halogen, methyl, halogenmethyl, cyano, methoxy or halogen-methoxy. In still another embodiment the present invention provides compounds of formula I wherein $R^{1.1}$ and $R^{1.2}$ are hydrogen and $R^1$ is fluoro, e.g. 2-fluoro, 3-fluoro or 4-fluoro, chloro, e.g. 3-chloro, methyl, e.g. 4-methyl, halogenmethyl, e.g. 3-trifluoromethyl, cyano, methoxy, e.g. 2-methoxy, 3-methoxy or 4-methoxy, or halogen-methoxy, e.g. 3-trifluoromethoxy. In another embodiment the present invention provides compounds of formula I wherein $R^1$, $R^{1.1}$ and $R^{1.2}$ are hydrogen.

In another aspect the present invention provides compounds of formula I wherein $R^{21}$, $R^{22}$ and $R^{23}$ are hydrogen.

In still another aspect the present invention provides compounds of formula I wherein $R^{24}$ is hydrogen.

In still another aspect the present invention provides compounds of formula I wherein $R^3$ is —$NHR^6$ wherein $R^6$ is —C(O)H, —C(O)—$CH_3$, —C(O)—$CH_2F$, —C(O)—$CHF_2$, —C(O)—$CF_3$, —C(O)O—$CH_3$, —C(O)—$NH_2$ or —$SO_2$—$CH_3$.

In one aspect the present invention provides compounds of formula I wherein the compounds have (S)-configuration.

In another aspect the present invention provides compounds of formula I wherein Q is =C($R^{24}$)—, wherein $R^{24}$ is hydrogen, X—Y is —$CH_2$—O—; $R^{1.1}$ and $R^{1.2}$ are hydrogen; $R^1$ is hydrogen or halogen; $R^{21}$, $R^{22}$ and $R^{23}$ are hydrogen; $R^3$ is —$NHR^6$; $R^4$ is hydrogen; and $R^6$ is —C(O)H, —C(O)—$(C_1-C_3)$-alkyl, C(O)-halogen-$(C_1-C_3)$alkyl, —C(O)O$(C_1-C_3)$-alkyl, —C(O)$NH_2$ or —$SO_2$—$(C_1-C_3)$-alkyl. In still another aspect the present invention provides compounds of formula I wherein Q is =C($R^{24}$)—, wherein $R^{24}$ is hydrogen, X—Y is —$CH_2$—O—; $R^{1.1}$ and $R^{1.2}$ are hydrogen; $R^1$ is hydrogen or halogen; $R^{21}$, $R^{22}$ and $R^{23}$ are hydrogen; $R^3$ is —$NHR^6$; $R^4$ is hydrogen; and $R^6$ is —C(O)H, —C(O)—$CH_3$, —C(O)—$CH_2F$, —C(O)—$CHF_2$, —C(O)—$CF_3$, —C(O)O—$CH_3$, —C(O)—$NH_2$ or —$SO_2$—$CH_3$.

Examples of compounds of formula I include compounds selected from
(RS)-N-{1-[4-(3-fluoro-benzyloxy)-phenyl]-5-oxo-pyrrolidin-3-yl}-acetamide,
(S)-N-{1-[4-(3-fluoro-benzyloxy)-phenyl]-5-oxo-pyrrolidin-3-yl}-acetamide,
(R)-N-{1-[4-(3-fluoro-benzyloxy)-phenyl]-5-oxo-pyrrolidin-3-yl}-acetamide,
(RS)-N-{1-[4-(3-fluoro-benzyloxy)-phenyl]-5-oxo-pyrrolidin-3-yl}-formamide,
(S)-N-{1-[4-(3-fluoro-benzyloxy)-phenyl]-5-oxo-pyrrolidin-3-yl}-formamide,
(R)-N-{1-[4-(3-fluoro-benzyloxy)-phenyl]-5-oxo-pyrrolidin-3-yl}-formamide,
(RS)-{1-[4-(3-fluoro-benzyloxy)-phenyl]-5-oxo-pyrrolidin-3-yl}-carbamic acid methyl ester,
(RS)-{1-[4-(3-fluoro-benzyloxy)-phenyl]-5-oxo-pyrrolidin-3-yl}-urea,
(RS)-N-{1-[4-(3-fluoro-benzyloxy)-phenyl]-5-oxo-pyrrolidin-3-yl}-methanesulfonamide,
(S)-2-fluoro-N-{1-[4-(3-fluoro-benzyloxy)-phenyl]-5-oxo-pyrrolidin-3-yl}-acetamide,
(S)-2,2-difluoro-N-{1-[4-(3-fluoro-benzyloxy)-phenyl]-5-oxo-pyrrolidin-3-yl}-acetamide,
(S)-2,2,2-trifluoro-N-{1-[4-(3-fluoro-benzyloxy)-phenyl]-5-oxo-pyrrolidin-3-yl}-acetamide,
(RS)-N-{1-[4-(4-fluoro-benzyloxy)-phenyl]-5-oxo-pyrrolidin-3-yl}-acetamide,
(R)-N-{1-[4-(4-fluoro-benzyloxy)-phenyl]-5-oxo-pyrrolidin-3-yl}-acetamide,
(S)-N-{1-[4-(4-fluoro-benzyloxy)-phenyl]-5-oxo-pyrrolidin-3-yl}-acetamide,
(RS)-N-{1-[4-(4-fluoro-benzyloxy)-phenyl]-5-oxo-pyrrolidin-3-yl}-formamide,
(RS)-N-[1-(4-benzyloxy-phenyl)-5-oxo-pyrrolidin-3-yl]-acetamide,
(RS)-N-{1-[4-(2-fluoro-benzyloxy-phenyl]-5-oxo-pyrrolidin-3-yl}-acetamide,
(RS)-(E)-N-(1-{4-[2-(3-fluoro-phenyl)-vinyl]-phenyl}-5-oxo-pyrrolidin-3-yl)-acetamide,
(RS)-N-(1-{4-[2-(3-fluoro-phenyl)-ethyl]-phenyl}-5-oxo-pyrrolidin-3-yl)-acetamide,
(RS)-N-{1-[6-(4-fluoro-benzyloxy)-pyridin-3-yl]-5-oxo-pyrrolidin-3-yl}-acetamide,
(S)-N-{1-[4-(3-chloro-benzyloxy)-phenyl]-5-oxo-pyrrolidin-3-yl}-acetamide,
(S)-N-{1-[4-(2,6-difluoro-benzyloxy)-phenyl]-5-oxo-pyrrolidin-3-yl}-acetamide,
(S)-N-{5-oxo-1-[4-(2,4,6-trifluoro-benzyloxy)-phenyl]-pyrrolidin-3-yl}-acetamide,
(S)-N-{1-[4-(3-methoxy-benzyloxy)-phenyl]-5-oxo-pyrrolidin-3-yl}-acetamide,
(S)-N-{5-oxo-1-[4-(4-trifluoromethyl-benzyloxy)-phenyl]-pyrrolidin-3-yl}-acetamide,
(S)-N-{1-[4-(4-methyl-benzyloxy)-phenyl]-5-oxo-pyrrolidin-3-yl}-acetamide and
(S)-N-{1-[4-(3-cyano-benzyloxy)-phenyl]-5-oxo-pyrrolidin-3-yl}-acetamide.

In another embodiment the present invention provides a process for the preparation of compounds of formula I comprising reacting a compound of formula II

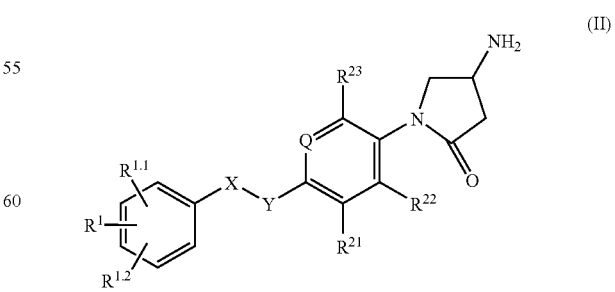

with an isocyanate or an acyl donating agent of formula Z-C(O)—$(C_1-C_3)$-alkyl, Z-C(O)-halogen-$(C_1-C_3)$alkyl, Z-C(O)O($C_1$–$C_3$)-alkyl, or Z-$SO_2$—($C_1$–$C_3$)-alkyl wherein Z is an activating group, e.g. halogen or anhydride.

All starting materials employed in the processes described herein are either commercially available or can be prepared by conventional means.

Scheme 1 shows the main routes to compounds of the formula I. The intermediates III and IIIa may be reacted with itaconic acid IV neat at a temperature in the range of from 80° C. to 200° C.

The compounds of formula Va may be alkylated by Williamson-ether synthesis using an unsubstituted or substituted benzyl derivative selected from benzylic halides, tosylates, methane sulfonates (mesylates) and trifluoromethane sulfonates (triflates). Bases used can be, e.g. alcoholates or carbonates, like sodium, potassium or cesium carbonate.

Preferred solvents are lower alcohols, acetonitrile or lower ketones at a temperature in the range of from 20° C. and reflux temperature.

Another approach is the Mitsunobu-coupling: an optionally substituted benzylic alcohol is reacted with a compound of formula Va in an inert solvent, e.g., diethyl ether or tetrahydrofurane, using dialkyl-azo-dicarboxylates in the presence of phosphines, e.g., tributyl- or triphenyl-phosphine. The hydrolysis of compounds of formula Va can be performed by methods known per se like hydrolysis under acidic conditions, e.g. with hydrochloric acid, or basic conditions, e.g. lithium, sodium- or potassium hydroxide in mixtures of alcohols and water as the solvent.

Compounds of formula II and IIa can be obtained starting from acid derivatives of formula V by nucleophilic migrations from a carbon to a nitrogen atom, such as e.g. by Hofmann or Curtius rearrangement, via the formation of the corresponding isocyanate. Subsequent treatment of the isocyanate by aqueous acid directly yields amines of formula II. Treatment of the intermediate isocyanate with suitable alcohols gives the protected amino derivatives of formula IIa. For the treatment of the isocyanate, alcohols are selected which yield the typical carbamates used as amine protecting groups, e.g. tert-butoxycarbonyl, benzyloxycarbonyl, or fluorenylmethoxycarbonyl. Their cleavage to the amine to yield compounds of formula II follows the protocols which are well known from the literature.

The further transformation to compounds of formula II can be performed by standard procedures, such as e.g. by reaction with activated acyl derivatives, e.g. acyl halogenides or anhydrides, or by condensation reactions of the acid using e.g. carbodiimides as condensation reagent or by reaction with isocyanates.

In compounds of formula I or IIa wherein —X—Y— has the meaning of —$CH_2$—O—, the optionally substituted benzyl residue can function as a transient group which can be cleaved by hydrogenolysis. The resulting compounds of formula VIa or VIb can then be re-alkylated by a different benzyl group under the aforementioned conditions. As known to those skilled in the art, this process is only possible on condition that $R^{6*}$ and PG (protecting group) are groups that are stable under the aforementioned reaction conditions for the hydrogenolysis and alkylation reaction, eg. formyl or acetyl for $R^{6*}$, tert-butoxycarbonyl (BOC) for PG.

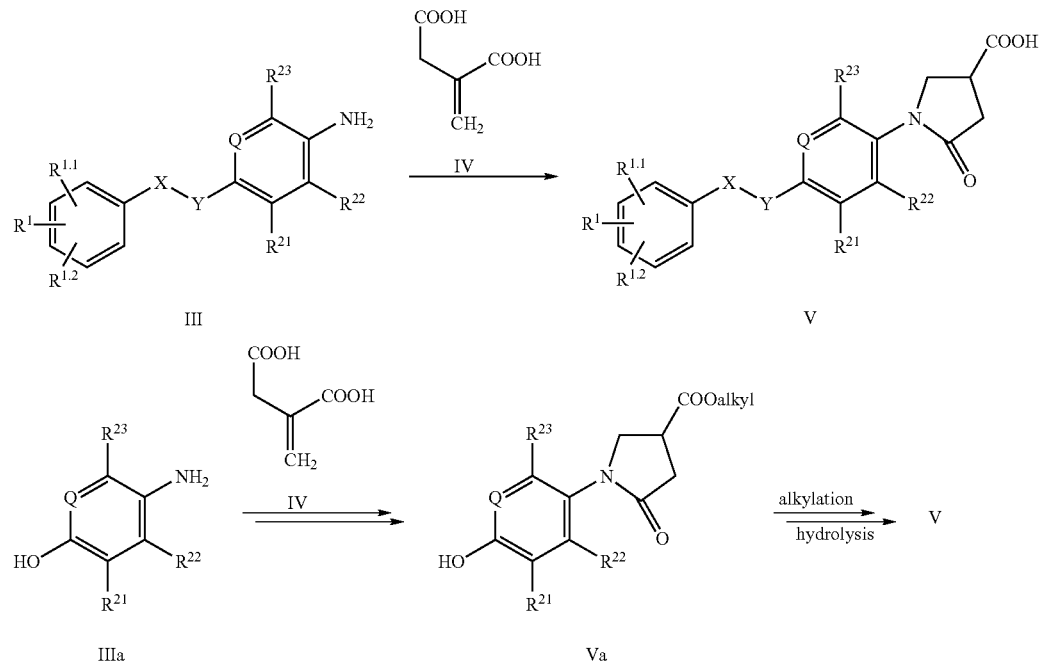

-continued
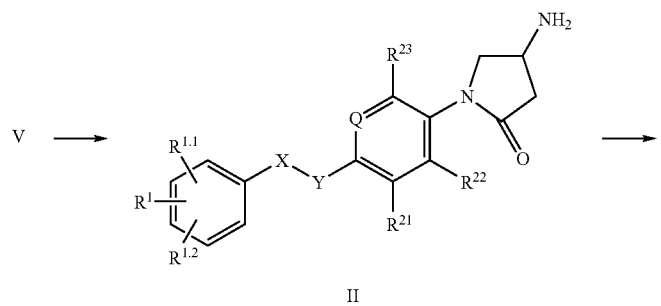
II
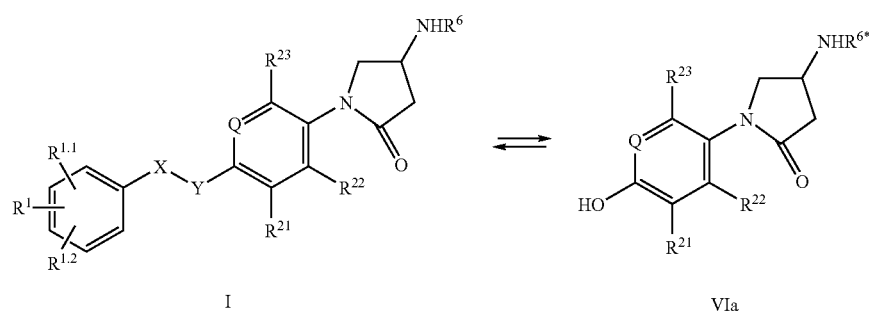
I                    VIa
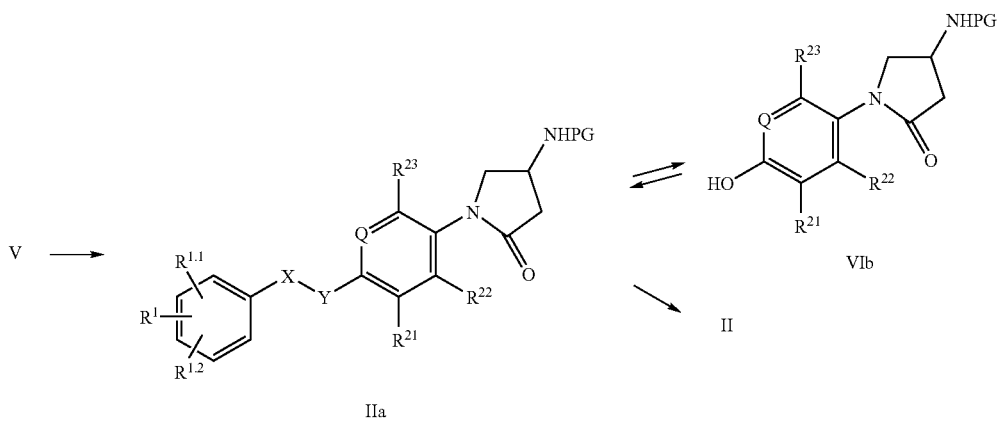
IIa                    VIb Another method to prepare compounds of formula I involves cross-coupling reactions of arylstannanes [Lam et al., Tetrahedron Lett. 43:3091 (2002)], arylboronates [Lam et al., Synlett 5:674 (2000); Chan et al., Tetrahedron Lett. 39:2933 (1998)] or aryl halides [Buchwald et al., J. Amer. Chem. Soc. 118:7215 (1996)] with the corresponding pyrrolidones (scheme 2).

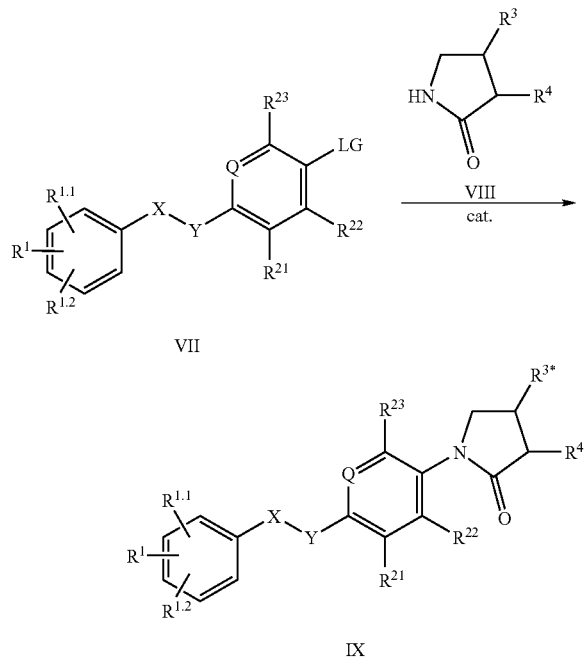

Scheme 2 wherein LG is a leaving group, e.g. halogen, e.g. Cl, Br or I, or $SnR_3$ or $B(OH)_2$ and $R^{3*}$ is —$NHR^6$ or alkoxycarbonyl.

In accordance with the present invention, one method to prepare compounds of general formula III wherein —X—Y— is —$CH_2$—O—, i.e. compounds of formula IIIb, is shown in scheme 3: The intermediates of formula XII are accessible through nucleophilic substitution of aromatic nitro compounds of formula XI containing p-substituted leaving groups with benzylic alcohols of formula X. Examples for leaving groups in para-position are halogens (F, Cl, Br, I), tosylates, mesylates or triflates. These substitution reactions can be conducted neat or in inert solvents like toluene or xylene. A preferred reaction temperature is in the range of from 50° C. to 150° C. Alternatively, compounds of formula XII can be prepared by Williamson-ether synthesis, starting from p-nitrophenols of formula XIV and benzylic halides, tosylates, mesylates or triflates of formula XIII. Bases used can be for example alcoholates or carbonates (sodium, potassium or cesium carbonate). Preferred solvents are lower alcohols, acetonitrile or lower ketones at a temperature in the range of from 20° C. to reflux temperature. Another approach is the Mitsunobu-coupling of benzylic alcohols with p-nitrophenols of formula XIV. The reaction is done as usual in inert solvents, for example, diethyl ether or tetrahydrofurane, using dialkyl-azo-dicarboxylates in the presence of phosphines, e.g. tributyl- or triphenyl-phosphine.

The key intermediates of formula XII are reduced to the amino-compounds IIIb using catalytic hydrogenation, e.g. using platinum on charcoal as the catalyst in lower alcohols, ethyl acetate or tetrahydrofurane. An alternative is the reduction of the nitro-group by metals like iron, tin, or zinc in acidic media like diluted hydrochloric acid or acetic acid. Metals can also be replaced by metal salts, e.g. tin-(II)-chloride.

Scheme 3

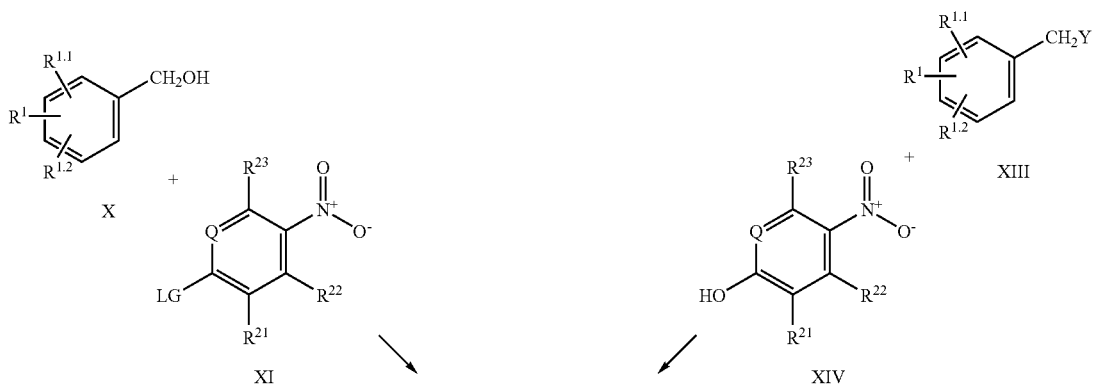

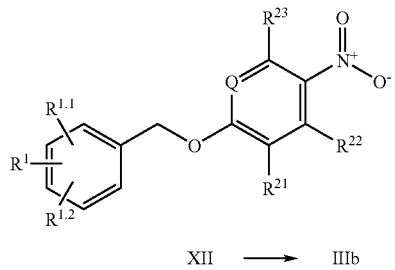

XII → IIIb wherein LG is a leaving group, e.g. halogen, OTf, etc., and Y is a leaving group, e.g. halogen, OTf, etc. or OH (for Mitsunobu-coupling).

The intermediates of formula III wherein —X—Y— is —CH=CH—, i.e. compound of formula IIIc, or wherein —X—Y— is —CH$_2$—CH$_2$—, i.e. compound of formula IIId, may be prepared by a procedure which is shown in scheme 4. The intermediates of formula XVII are accessible by olefination reaction of optionally substituted aromatic aldehydes of formula XV with dialkyl-(4-nitrobenzyl)-phosphonates of formula XVI in the presence of a base, e.g. sodium hydride, yielding the corresponding nitro-olefins of formula XVII.

The key intermediates of formula XVII can be reduced selectively to the amino-olefin of formula IIIc by metals or metal salts, e.g., tin-(II)-chloride or by catalytic hydrogenation, e.g., using platinum on charcoal as the catalyst in lower alcohols, ethyl acetate or tetrahydrofurane as the solvent. The amino derivatives of formula IIId can be obtained from the nitro derivatives of formula XVII or the amino-olefins of formula IIIc by hydrogenation using palladium on charcoal as the catalyst in lower alcohols, ethyl acetate or tetrahydrofurane as the solvent.

Compounds of general formula I can also exist in optical pure form. Separation into antipodes can be affected according to methods known per se, either at an early stage of the synthesis starting with compounds of formula V by salt formation with an optically active amine such as, for example, (+)- or (−)-1-phenylethylamine or (+)− or (−)−1-naphthylethylamine and separation of the diastereomeric salts by fractional crystallisation or by derivatisation with a chiral auxiliary substance such as, for example, (+)- or (−)-2-butanol, (+)- or (−)-1-phenylethanol, or (+)- or (+)-menthol and separation of the diastereomeric products by chromatography and/or crystallisation and subsequent cleavage of the bond to the chiral auxiliary substance; or, on the very last stage, by separation of the enantiomers of formula I by chromatography on a chiral phase. Furthermore, compounds of formula I can also be obtained from enantiopure intermediates obtained by biotransformation, e.g. by hydrolysis of esters of formula Va by enzymes, such as e.g. cholesterase from *Candida cylindracea*. In order to determine the absolute configuration of the pyrrolidinone derivative obtained, the pure diastereomeric salts or deriva-

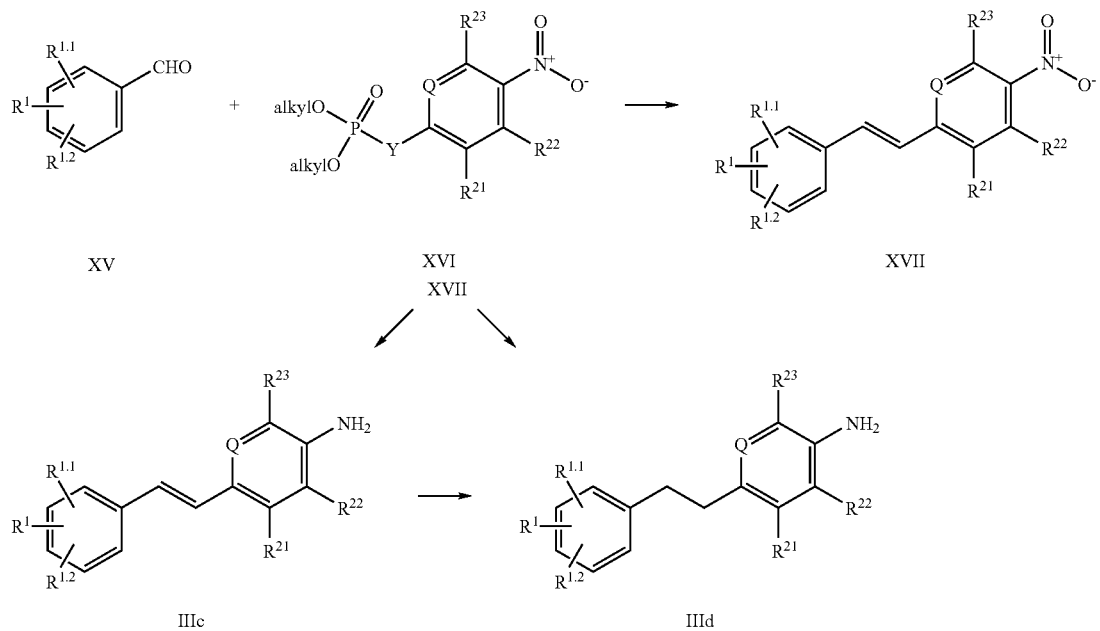

Scheme 4 tives can be analysed by conventional spectroscopic methods, with X-ray spectroscopy on single crystals being an especially suitable method.

The compounds of formula I are, as already mentioned above, monoamine oxidase B inhibitors and can be used for the treatment or prevention of diseases in which MAO-B inhibitors might be beneficial. These include acute and chronic neurological disorders, cognitive disorders and memory deficits. Treatable neurological disorders are for instance traumatic or chronic degenerative processes of the nervous system, such as Alzheimer's disease, other types of dementia, minimal cognitive impairment or Parkinson's disease. Other indications include psychiatric diseases such as depression, anxiety, panic attack, social phobia, schizophrenia, eating and metabolic disorders such as obesity, as well as the prevention and treatment of withdrawal syndromes induced by abuse of alcohol, nicotine and other addictive drugs. Other treatable indications may be peripheral neuropathy caused by cancer chemotherapy (WO 97/33,572), reward deficiency syndrome (WO 01/34,172), or the treatment of multiple sclerosis (WO 96/40,095), and other neuroinflammatory diseases.

The compounds of formula I are especially useful for the treatment and prevention of Alzheimer's disease and senile dementia.

The pharmacological activity of the compounds was tested using the following method:

The cDNAs encoding human MAO-A and MAO-B were transiently transfected into EBNA cells using the procedure described by Schlaeger and Christensen [Cytotechnology 15:1–13 (1998)]. After transfection, cells were homogenised by means of a Polytron homogenizer in 20 mM Tris HCl buffer, pH 8.0, containing 0.5 mM EGTA and 0.5 mM phenylmethanesulfonyl fluoride. Cell membranes were obtained by centrifugation at 45,000×g and, after two rinsing steps with 20 mM Tris HCl buffer, pH 8.0, containing 0.5 mM EGTA, membranes were eventually re-suspended in the above buffer and aliquots stored at −80° C. until use.

MAO-A and MAO-B enzymatic activity was assayed in 96-well-plates using a spectrophotometric assay adapted from the method described by Zhou and Panchuk-Voloshina [Analytical Biochemistry 253:169–174 (1997)]. Briefly, membrane aliquots were incubated in 0.1 M potassium phosphate buffer, pH 7.4, for 30 min at 37° C. containing different concentrations of the compounds. After this period, the enzymatic reaction was started by the addition of the MAO substrate tyramine together with 1 U/ml horse-radish peroxidase (Roche Biochemicals) and 80 μM N-acetyl-3,7-dihydroxyphenoxazine (Amplex Red, Molecular Probes). The samples were further incubated for 30 min at 37° C. in a final volume of 200 μl and absorbance was then determined at a wavelength of 570 nm using a SpectraMax plate reader (Molecular Devices). Background (non-specific) absorbance was determined in the presence of 10 μM clorgyline for MAO-A or 10 μM L-deprenyl for MAO-B. $IC_{50}$ values were determined from inhibition curves obtained using nine inhibitor concentrations in duplicate, by fitting data to a four parameter logistic equation using a computer program.

The compounds of the present invention are specific MAO-B inhibitors. The $IC_{50}$ values of preferred compounds of formula I as measured in the assay described above are in the range of 1 μM or less, typically 0.1 μM or less, and ideally 0.02 μM or less.

The present invention also provides pharmaceutical compositions containing Active Compounds, or pharmaceutically acceptable salts thereof, and a pharmaceutically acceptable carrier. Active Compounds include individual isomers and racemic and non-racemic mixtures thereof. Such pharmaceutical compositions can be in the form of tablets, coated tablets, dragees, hard and soft gelatine capsules, solutions, emulsions or suspensions. The pharmaceutical compositions also can be in the form of suppositories or injectable solutions.

The pharmaceutical compositions of the invention, in addition to one or more Active Compounds, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They may also contain other therapeutically valuable substances.

Compounds of the invention are selective MAO-B inhibitors. Therefore, the present invention also provides methods of treating or preventing diseases that are mediated by monoamine oxidase B. Such methods include administering a therapeutically effective amount of an Active Compound, for example, a compound of formula I or I*, or a pharmaceutically acceptable salt thereof, to an individual in need of such treatment. In one embodiment, the invention provides a method for the treatment or prevention of Alzheimer's disease by administering to an individual a therapeutically effective amount of an Active Compound, e.g., a compound of formula I or I*. In another embodiment, the present invention provides a method for the treatment or prevention of senile dementia by administering to an individual a therapeutically effective amount of an Active Compound, e.g., a compound of formula I or I*.

The compounds and compositions of the present invention can be administered in a conventional manner, for example, orally, rectally, or parenterally. The pharmaceutical compositions of the invention can be administered orally, for example, in the form of tablets, coated tablets, dragees, hard and soft gelatine capsules, solutions, emulsions, or suspensions. The pharmaceutical compositions also can be administered rectally, for example, in the form of suppositories, or parenterally, for example, in the form of injection solutions.

The dosage at which the Active Compound is administered can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

The following examples are provided for illustration of the invention. They should not be considered as limiting the scope of the invention, but merely as being representative thereof. Unless otherwise indicated, the following examples have been performed, regardless of the tense in which they are written. The abbreviation "RT" means "room temperature."

EXAMPLE 1

(RS)-N-{1-[4-(3-Fluoro-benzyloxy)-phenyl]-5-oxo-pyrrolidin-3-yl}-acetamide a) (RS)-1-(4-Benzyloxy-phenyl)-5-oxo-pyrrolidine-3-carboxylic acid 18.8 g (94.4 mmol) of 4-benzyloxyaniline are mixed with 12.28 g (94.4 mmol) itaconic acid. The solid mixture is heated to 130° C. After 20 min the molten material solidifies. After cooling, the resulting solid is triturated with ethyl acetate to yield 28.26 g (96% of theory) of (RS)-1-(4-benzyloxy-phenyl)-5-oxo-pyrrolidine-3-carboxylic acid as a greyish solid. MS: m/e=311 (M)$^+$.

b) (RS)-1-[4-Benzyloxy)-phenyl]-5-oxo-pyrrolidine-carbonyl chloride

A suspension of 9.50 g (30.5 mmol) of (RS)-1-[4-(3-benzyloxy)-phenyl]-5-oxo-pyrrolidine-3-carboxylic acid in 100 ml of dichloromethane is treated with 13.3 ml (183 mmol) of thionylchloride at RT during 18 hours. For the working-up, the reaction mixture is evaporated under reduced pressure to dryness, then the residue is dispersed in toluene and evaporated to dryness again to yield quantitatively the (RS)-1-[4-benzyloxy)-phenyl]-5-oxo-pyrrolidine-carbonyl chloride as a yellowish solid which is used in the next step without further purification and characterisation.

c) (RS)-[1-(4-Benzyloxy-phenyl)-5-oxo-pyrrolidin-3-yl]-carbamic acid tert-butyl ester A solution of 0.20 g (0.6 mmol) of(RS)-1-(4-benzyloxy-phenyl)-5-oxo-pyrrolidine-3-carbonyl chloride in 12 ml of toluene is cooled to 0° C. and 0.058 g (0.9 mmol) of sodium azide are added. The reaction mixture is warmed to RT and stirring continued or 1 h. Thereafter, the mixture is heated to 80° C., 1.88 ml (20 mmol) of tert-butanol are added and stirring continued for 1 h. For the working-up, the mixture is cooled, diluted with ethyl acetate and, consecutively, extracted with saturated sodium hydrogencarbonate solution, water and brine. The organic phase is dried over sodium sulfate and evaporated under reduced pressure to yield the crude compound as a brownish solid. For purification, the material obtained is chromatographed on silica gel using a 2:1 mixture of n-hexane and ethyl acetate as the eluent. There are obtained 0.13 g (55% of theory) of (RS)-[1-(4-benzyloxy-phenyl)-5-oxo-pyrrolidin-3-yl]-carbamic acid tert-butyl ester as a white solid. MS: m/e=400 (M+NH$_4$)$^+$.

d) (RS)-[1-(4-Hydroxy-phenyl)-5-oxo-pyrrolidin-3-yl]-carbamic acid tert-butyl ester A solution of 82 mg (0.2 mmol) of (RS)-[1-(4-benzyloxy-phenyl)-5-oxo-pyrrolidin-3-yl]-carbamic acid tert-butyl ester in 2 ml of THF is hydrogenated in presence of 7 mg palladium on carbon (10%) at ambient pressure and RT during 18 h. For the working-up, the reaction mixture is filtered over Dicalit, then evaporated under reduced pressure. The crude (RS)-[1-(4-hydroxy-phenyl)-5-oxo-pyrrolidin-3-yl]-carbamic acid tert-butyl ester is obtained as a colorless oil, which is directly engaged in the next step without further purification and characterisation.

e) (RS)-{1-[4-(3-Fluoro-benzyloxy)-phenyl]-5-oxo-pyrrolidin-3-yl}-carbamic acid tert-butyl ester A solution of 62 mg (0.21 mmol) of the crude (RS)-[1-(4-hydroxy-phenyl)-5-oxo-pyrrolidin-3-yl]-carbamic acid tert-butyl ester in 3 ml of 2-butanone is treated with 0.031 ml (0.23 mmol) of 3-fluorobenzyl-bromide and 59 mg (0.42 mmol) of potassium carbonate and the mixture is stirred at 50° C. for 18 h. For the working-up, the reaction mixture is diluted with ethyl acetate and extracted with water. The organic phase is dried over sodium sulfate and evaporated under reduced pressure. For purification, the material obtained is chromatographed on silica gel using a 2:1 mixture of n-hexane and ethyl acetate as the eluent. There are obtained 61 mg (72% of theory) of (RS)-{1-[4-(3-fluoro-benzyloxy)-phenyl]-5-oxo-pyrrolidin-3-yl}-carbamic acid tert-butyl ester as a white solid. MS: m/e=401 (M+H)$^+$.

f) (RS)-4-Amino-1-[4-(3-fluoro-benzyloxy)-phenyl]-pyrrolidin-2-one hydrochloride A solution of 49 mg (0.12 mmol) of(RS)-{1-[4-(3-fluoro-benzyloxy)-phenyl]-5-oxo-pyrrolidin-3-yl}-carbamic acid tert-butyl ester in 1 ml of dioxane is treated with 0.10 ml of hydrochloric acid (37%). The yellowish solution is warmed to 45° C. for 1 h. For the working-up, the reaction mixture is evaporated under reduced pressure and the solid residue is triturated with ether. After filtration and drying, 33 mg (79% of theory) of (RS)-4-amino-1-[4-(3-fluoro-benzyloxy)-phenyl]-pyrrolidin-2-one hydrochloride are obtained as a white solid. MS: m/e=301 (M+H)$^+$.

g) (RS)-N-{1-[4-(3-Fluoro-benzyloxy)-phenyl]-5-oxo-pyrrolidin-3-yl}-acetamide

A solution of 25 mg (0.07 mmol) of (RS)-4-amino-1-[4-(3-fluoro-benzyloxy)-phenyl]-pyrrolidin-2-one hydrochloride in 1 ml of dichloromethane is treated with 22 μl (0.16 mmol) of triethylamine and cooled to 0° C. To this solution, 6 μl (0.08 mmol) of acetylchloride are added and stirring at 0° C. is continued for 30 min. For the working-up, the reaction mixture is treated with 2 ml of ammonium hydroxide solution, the organic phase separated, thereafter dried over sodium sulfate and evaporated under reduced pressure. For purification, the material obtained is chromatographed on silica gel using a 95:5 mixture of dichloromethane and methanol as the eluent. There are obtained 20 mg (78% of theory) of (RS)-N-{1-[4-(3-fluoro-benzyloxy)-phenyl]-5-oxo-pyrrolidin-3-yl}-acetamide as a white solid. MS: m/e=343 (M+H)$^+$.

EXAMPLE 2

(S)-N-{1-[4-(3-Fluoro-benzyloxy)-phenyl]-5-oxo-pyrrolidin-3-yl}-acetamide a) (RS)-1-(4-Hydroxyoxy-phenyl)-5-oxo-pyrrolidine-3-carboxylic acid In a metallic pan, 257.0 g (2.355 mol) of 4-aminophenol and 301.75 g (2.32 mol) of itaconic acid are mixed in solid form. Under stirring with a metal spatula, the mixture is carefully heated on a heating plate. At 110–120° C. the exothermic reaction starts under boiling and, while the temperature raises to 150° C., the reaction mass turns to a beige solid. The sandy product is left to cool down to RT within 1–2 hours. The crude (RS)-1-(4-hydroxyoxy-phenyl)-5-oxo-pyrrolidine-3-carboxylic acid is engaged in the next step without further purification or characterisation.

b) (RS)-1-(4-Hydroxy-phenyl)-5-oxo-pyrrolidine-3-carboxylic acid methyl ester

In a 101 4-necked flask equipped with a reflux condenser, a thermometer, and a mechanical stirrer, the crude (RS)-1-(4-hydroxy-phenyl)-5-oxo-pyrrolidine-3-carboxylic acid is dissolved in a mixture of 5000 ml of methanol, 24 ml of concentrated sulfuric acid and 400 ml of 2,2-dimethoxypropane and stirred under reflux during 2 h. For the working-up, the reaction solution is reduced to half of its volume by distillation, then transferred into a 20 l vessel. Under stirring at 40° C., a mixture of 2500 ml of water/ice (1:1) is added. Crystallisation starts immediately, and, thereupon, the fine white crystals are collected on a filter funnel. They are washed with a total of 2000 ml of cold water until the filtrate becomes colorless and neutral. The well pressed and pre-dried product from the filter funnel is dried under reduced pressure to yield 980 g (84% of theory, 2 steps) of the (RS)-1-(4-hydroxyoxy-phenyl)-5-oxo-pyrrolidine-3-carboxylic acid methyl ester as a white solid; MS: m/e=234 $(M+H)^+$.

c) (R)-1-(4-Hydroxy-phenyl)-5-oxo-pyrrolidine-3-carboxylic acid methyl ester and (S)-1-(4-hydroxy-phenyl)-5-oxo-pyrrolidine-3-carboxylic acid A suspension of 50.22 g (213.5 mmol) (RS)-1-(4-hydroxy-phenyl)-5-oxo-pyrrolidine-3-carboxylic acid methyl ester (98% HPLC) in 500 ml cyclohexane is stirred moderately. By the addition of 2.01 0.1M sodium chloride, 5 mM magnesium sulfate, 3 mM potassium phosphate buffer pH 6.0 an emulsion/suspension is formed and re-adjusted to pH 6.0. The temperature is set to 30° C. Hydrolysis is started by the addition of 201 mg of cholesterase from *Candida cylindracea* (Roche Applied Science, Industrial Products, Enzyme Projects, Sandhofer Str. 116, D-68305 Mannheim, Germany, order no. 10129046103) and the pH kept constant at 6.0 by the controlled addition of 0.1N NaOH-solution (pH-stat) under moderate stirring. After a total consumption of 1016 ml of titrating agent (overnight; 48.6% conversion) the reaction mixture is extracted with 3.5 l and 2×2.5 l dichloromethane and subsequently with 3.5 l ethyl acetate. The combined dichloromethane phases are dried on sodium sulfate, evaporated and dried on HV to give 22.5 g (95.6 mmol; 44.8%) white crystals of ethyl (R)-1-(4-hydroxy-phenyl)-5-oxo-pyrrolidine-3-carboxylate; purity: HPLC: >99%; optical integrity: 96.3% e.e.; $[\alpha]_D=-27.7°$ (c=1.02; EtOH); MS: 235.1.

The aqueous phase is adjusted to pH 2.2 with 32% hydrochloric acid and extracted with 3×3.5 l ethyl acetate. The combined organic phases are dried on sodium sulfate, evaporated and dried on HV to give 21.9 g (99.0 mmol; 46.4%) of (S)-1-(4-hydroxy-phenyl)-5-oxo-pyrrolidine-3-carboxylic acid; purity HPLC: >99%; optical integrity 99.1% e.e.; $[\alpha]_D=25.4°$ (c=1.05; EtOH); MS: 221.1.

d) (S)-1-(4-Hydroxy-phenyl)-5-oxo-pyrrolidine-3-carboxylic acid methyl ester

A mixture of 26 g (117.5 mmol) of (S)-1-(4-hydroxy-phenyl)-5-oxo-pyrrolidine-3-carboxylic acid, 0.66 ml of sulfuric acid, and 100 ml of dimethoxypropane in 700 ml of methanol are heated to reflux for 3 hours. For the working-up, the reaction mixture is reduced to ⅘ of its volume, then the residue is added under stirring to a mixture of ice and water. The precipitated product is collected on a filter funnel, washed with cold water and finally dried under high vacuum to yield 23.7 g (86% of theory) of (S)-1-(4-hydroxy-phenyl)-5-oxo-pyrrolidine-3-carboxylic acid methyl ester as a white solid; MS: m/e=234 $(M–H)^+$; optical integrity: 97.4% e.e. .

e) (S)-1-[4-(3-Fluoro-benzyloxy)-phenyl]-5-oxo-pyrrolidine-3-carboxylic acid methyl ester A solution 14.23 g (110.6 mmol) of 3-fluoro-benzylalcohol and 27.19 g (108.8 mmol) of triphenylphosphine in 150 ml of tetrahydrofurane is added dropwise within 50 min under a nitrogen atmosphere at 0° C. to a solution of 23.65 g (100.5 mmol) of (S)-1-(4-hydroxy-phenyl)-5-oxo-pyrrolidine-3-carboxylic acid methyl ester and 21.62 g (100.5 mmol) of diisopropyl azodicarboxylate in 200 ml of tetrahydrofurane. The mixture is left to warm to RT and stirring is continued for 18 hours. For the working-up, the mixture is evaporated under reduced pressure. The solid residue is triturated in 400 ml of ether to leave a white solid mainly consisting of the product and triphenylphosphinoxide. After filtration, the solid material is triturated in 100 ml of cold methanol to yield 23.5 g (68% of theory) of (S)-1-[4-(3-fluoro-benzyloxy)-phenyl]-5-oxo-pyrrolidine-3-carboxylic acid methyl ester as a white solid [MS: m/e=344 $(M+H)^+$] together with traces of triphenylphosphine and diisopropyl hydrazodicarboxylate.

f) (S)-1-[4-(3-Fluoro-benzyloxy)-phenyl]-5-oxo-pyrrolidine-3-carboxylic acid

A solution of 25.61 g (74.6 mmol) of (S)-1-[4-(3-fluoro-benzyloxy)-phenyl]-5-oxo-pyrrolidine-3-carboxylic acid methyl ester in 650 ml of dioxane is treated with 175 ml of hydrochloric acid (37%). The mixture is heated at 50° C. for 18 h in a closed flask. For the working-up, the solution is evaporated under reduced pressure to yield the crude acid as a yellow solid. For purification, the crude acid is triturated at 0° C. in 50 ml of ethyl acetate. The solid is collected on a filter funnel and then dried under high vacuum to yield 20.3 g (82% of theory) of (S)-1-[4-(3-fluoro-benzyloxy)-phenyl]-5-oxo-pyrrolidine-3-carboxylic acid as a yellowish solid; MS: m/e=330 $(M+H)^+$.

g) (S)-4-Amino-1-[4-(3-fluoro-benzyloxy)-phenyl]-pyrrolidin-2-one hydrochloride

A solution of 20.0 g (61 mmol) of (S)-1-[4-(3-fluoro-benzyloxy)-phenyl]-5-oxo-pyrrolidine-3-carboxylic acid in 300 ml of dioxane is treated with 6.7 ml (61 mmol) of N-methylmorpholine. Thereafter, the reaction mixture is cooled to −8° C. and 8.14 ml (61 mmol) of isobutyl chloroformate are added. After stirring for 5 min, a solution of 7.98 g (121 mmol) of sodium azide in 40 ml water are added while the temperature rises to 0° C. After stirring for 70 min at 0° C., the suspension is filtered over Dicalit. The filtrate is diluted with 700 ml of toluene and transferred into a separatory funnel. The organic layer is separated, then washed twice with 250 ml of a saturated solution of sodium hydrogencarbonate and twice with 200 ml of a saturated solution of sodium chloride.

Thereafter, the organic layer is dried over sodium sulfate and, after addition of 400 ml of toluene, the solvent and the residual isobutylalcohol are evaporated to end with a volume of about 350 ml. The solution is heated gradually to 80° C. and kept at this temperature for 70 min. After cooling, the solution of the intermediate isocyanate is concentrated to about 300 ml and is added dropwise to a solution of 25.4 ml of hydrochloric acid (37%) in 100 ml of dioxane while heating to 45° C. Finally, after complete addition, the temperature is raised to 60° C. for 1 hour and the hydrochloride already starts to precipitate. The mixture is cooled to 0° C. and the solid material formed is collected on a filter funnel. After washing with tert-butylmethylether, the product is dried under high vacuum. There are obtained 14.6 g (71% of theory) of (S)-4-amino-1-[4-(3-fluoro-benzyloxy)-phenyl]-pyrrolidin-2-one hydrochloride as a white solid. MS: m/e=301 (M+H)$^+$.

h) (S)-N-{1-[4-(3-Fluoro-benzyloxy)-phenyl]-5-oxo-pyrrolidin-3-yl}-acetamide

In an analogous manner to that described in Example 1 g), the acetylation of (S)-4-amino-1-[4-(3-fluoro-benzyloxy)-phenyl]-pyrrolidin-2-one hydrochloride yields the (S)-N-{1-[4-(3-fluoro-benzyloxy)-phenyl]-5-oxo-pyrrolidin-3-yl}-acetamide as a crystalline white solid. MS: m/e=343 (M+H)$^+$.

EXAMPLE 3

(R)-N-{1-[4-(3-Fluoro-benzyloxy)-phenyl]-5-oxo-pyrrolidin-3-yl}-acetamide a) (R)-1-[4-(3-Fluoro-benzyloxy)-phenyl]-5-oxo-pyrrolidine-3-carboxylic acid methyl ester In an analogous manner to that described in Example 2e), the alkylation of (R)-1-(4-hydroxy-phenyl)-5-oxo-pyrrolidine-3-carboxylic acid methyl ester [Example 2c)] with 3-fluorobenzylalcohol yields the (R)-1-[4-(3-fluoro-benzyloxy)-phenyl]-5-oxo-pyrrolidine-3-carboxylic acid methyl ester as a white solid. MS: m/e=344 (M+H)$^+$.

b) (R)-1-[4-(3-Fluoro-benzyloxy)-phenyl]-5-oxo-pyrrolidine-3-carboxylic acid

In an analogous manner to that described in Example 2f), the hydrolysis of (R)-1-[4-(3-fluoro-benzyloxy)-phenyl]-5-oxo-pyrrolidine-3-carboxylic acid methyl ester with hydrochloric acid (37%) in dioxane yields the (R)-1-[4-(3-fluoro-benzyloxy)-phenyl]-5-oxo-pyrrolidine-3-carboxylic acid as a white solid. MS: m/e=330 (M+H)$^+$.

c) (R)-4-Amino-1-[4-(3-fluoro-benzyloxy)-phenyl]-pyrrolidin-2-one hydrochloride

In an analogous manner to that described in Example 2 g), the Curtius rearrangement of (R)-1-[4-(3-fluoro-benzyloxy)-phenyl]-5-oxo-pyrrolidine-3-carboxylic acid yields the (R)-4-amino-1-[4-(3-fluoro-benzyloxy)-phenyl]-pyrrolidin-2-one hydrochloride as a white solid. MS: m/e=301 (M+H)$^+$.

d) (R)-N-{1-[4-(3-Fluoro-benzyloxy)-phenyl]-5-oxo-pyrrolidin-3-yl}-acetamide

In an analogous manner to that described in Example 1g), the acetylation of (R)-4-amino-1-[4-(3-fluoro-benzyloxy)-phenyl]-pyrrolidin-2-one hydrochloride yields the (R)-N-{1-[4-(3-fluoro-benzyloxy)-phenyl]-5-oxo-pyrrolidin-3-yl}-acetamide as a crystalline white solid. MS: m/e=343 (M+H)$^+$.

EXAMPLE 4

(RS)-N-{1-[4-(3-Fluoro-benzyloxy)-phenyl]-5-oxo-pyrrolidin-3-yl}-formamide

A mixture of 190 mg (1.9 mmol) of acetic acid anhydride and 108 mg (2.3 mmol) of formic acid is prepared at 0° C., then heated to 60° C. for 2 hours. After cooling to RT, the solution is diluted with 1 ml of dry tetrahydrofurane, before a solution of 215 mg (0.7 mmol) of (RS)-4-amino-1-[4-(3-fluoro-benzyloxy)-phenyl]-pyrrolidin-2-one [Example 1f)] in 2 ml of dichloromethane is added (the amine is obtained from the corresponding hydrochloride after treatment with triethylamine and extraction from a mixture of dichloromethane and water). The formed suspension is stirred for 1 hour. For the working-up, the reaction mixture is diluted with dichloromethane and washed twice with water. The organic layer is separated, dried over sodium sulfate and evaporated. There are obtained 126 mg (54% of theory) of (RS)-N-{1-[4-(3-fluoro-benzyloxy)-phenyl]-5-oxo-pyrrolidin-3-yl}-formamide as a white solid. MS: m/e=329 (M+H)$^+$.

EXAMPLE 5

(S)-N-{1-[4-(3-Fluoro-benzyloxy)-phenyl]-5-oxo-pyrrolidin-3-yl}-formamide

In an analogous manner to that described in Example 4, the acylation of (S)-4-amino-1-[4-(3-fluoro-benzyloxy)-phenyl]-pyrrolidin-2-one [Example 2g)] yields (S)-N-{1-[4-(3-fluoro-benzyloxy)-phenyl]-5-oxo-pyrrolidin-3-yl}-formamide as a white semi-solid (yield 81% of theory). MS: m/e=329 (M+H)$^+$.

EXAMPLE 6

(R)-N-{1-[4-(3-Fluoro-benzyloxy)-phenyl]-5-oxo-pyrrolidin-3-yl}-formamide

In an analogous manner to that described in Example 4, the acylation of (R)-4-amino-1-[4-(3-fluoro-benzyloxy)-phenyl]-pyrrolidin-2-one [Example 3c)] yields (R)-N-{1-[4-(3-fluoro-benzyloxy)-phenyl]-5-oxo-pyrrolidin-3-yl}-formamide as a light yellow solid (yield 94% of theory). MS: m/e=329 (M+H)$^+$.

EXAMPLE 7

(RS)-{1-[4-(3-Fluoro-benzyloxy)-phenyl]-5-oxo-pyrrolidin-3-yl}-carbamic acid methyl ester A solution of 250 mg (0.74 mmol) of (RS)-4-amino-1-[4-(3-fluoro-benzyloxy)-phenyl]-pyrrolidin-2-one hydrochloride [Example 1f)] in 12 ml of dichloromethane is cooled to 0° C. and successively treated with 226 μl (1.6 mmol) of triethylamine and 64 μl (0.8 mmol) of methyl chloroformate. The mixture is left to warm to RT and stirred for 1 hour. For the working-up, dichloromethane and water are added to the reaction mixture. The organic layer is separated, dried over sodium sulfate, and evaporated. There are obtained 203 mg (76% of theory) of (RS)-{1-[4-(3-fluoro-benzyloxy)-phenyl]-5-oxo-pyrrolidin-3-yl}-carbamic acid methyl ester as a white solid. MS: m/e=359 (M+H)$^+$.

EXAMPLE 8

(RS)-{1-[4-(3-Fluoro-benzyloxy)-phenyl]-5-oxo-pyrrolidin-3-yl}-urea

A solution of 250 mg (0.74 mmol) of (RS)-4-amino-1-[4-(3-fluoro-benzyloxy)-phenyl]-pyrrolidin-2-one hydrochloride [Example 1f)] in 2 ml of N,N-dimethylformamide is cooled to 0° C. and successively treated with 386 μl (2.2 mmol) of N-ethyl-diisopropylamine and 307 μl (2.2 mmol) of trimethylsilylisocyanate. The mixture is left to warm to RT and stirred for 4 hours. For the working-up, the reaction mixture is evaporated under reduced pressure. The red residue is dissolved in dichloromethane and the organic phase washed with water. After separation of the organic layer and drying over sodium sulfate, it is evaporated to give a red oil. For purification, the crude product is chromatographed on silica gel using a gradient of a 95:5- to 90:10-mixture of dichloromethane and methanol as the eluent. After the chromatography, in addition, the product is triturated in ethyl acetate and sodium hydrogencarbonate at RT. There are obtained 153 mg (60% of theory) of (RS)-{1-[4-(3-fluoro-benzyloxy)-phenyl]-5-oxo-pyrrolidin-3-yl}-urea as a white solid. MS: m/e=344 (M+H)$^+$.

EXAMPLE 9

(RS)-N-{1-[4-(3-Fluoro-benzyloxy)-phenyl]-5-oxo-pyrrolidin-3-yl}-methanesulfonamide A solution of 250 mg (0.74 mmol) of (RS)-4-amino-1-[4-(3-fluoro-benzyloxy)-phenyl]-pyrrolidin-2-one hydrochloride [Example 1f)] in 8 ml of dichloromethane is cooled to 0° C. and successively treated with 226 µl (2.2 mmol) of triethylamine and 64 µl (2.2 mmol) of methanesulfochloride. The mixture is stirred for 30 min at 0° C. For the working-up, the reaction mixture is washed twice with water, the organic layer is separated and dried over sodium sulfate. After evaporation of the solvent, the crude material is chromatographed on silica gel using a 98:2-mixture of dichloromethane and methanol as the eluent. There are obtained 235 mg (84% of theory) of (RS)-N-{1-[4-(3-fluoro-benzyloxy)-phenyl]-5-oxo-pyrrolidin-3-yl}-methanesulfonamide as a white solid. MS: m/e=377 (M–H)$^+$.

EXAMPLE 10

(S)-2-Fluoro-N-{1-[4-(3-fluoro-benzyloxy)-phenyl]-5-oxo-pyrrolidin-3-yl}-acetamide A solution of 100 mg (0.3 mmol) of (S)-4-amino-1-[4-(3-fluoro-benzyloxy)-phenyl]-pyrrolidin-2-one hydrochloride [Example 2g)] in 0.3 ml of N,N-dimethylformamide is treated successively with 100 µl (0.6 mmol) of N-ethyldiisopropylamine and 55 µl (0.6 mmol) of methyl fluoroacetate. The resulting beige suspension is heated to 50° C. for 18 hours. For the working-up, the reaction mixture is evaporated, thereafter, the residue is dissolved in dichloromethane and the solution washed with 1 ml of hydrochloric acid (1N). The organic layer is separated, dried over sodium sulfate, and evaporated. For purification, the crude product is chromatographed on silica gel using a 98:2-mixture of dichloromethane and methanol as the eluent. There are obtained 30 mg (28% of theory) of (S)-2-fluoro-N-{1-[4-(3-fluoro-benzyloxy)-phenyl]-5-oxo-pyrrolidin-3-yl}-acetamide as a white solid. MS: m/e=378 (M+NH$_4$)$^+$.

EXAMPLE 11

(S)-2,2-Difluoro-N-{1-[4-(3-fluoro-benzyloxy)-phenyl]-5-oxo-pyrrolidin-3-yl}-acetamide A solution of 103 mg (0.3 mmol) of (S)-4-amino-1-[4-(3-fluoro-benzyloxy)-phenyl]-pyrrolidin-2-one hydrochloride [Example 2g)] in 0.5 ml of N,N-dimethylformamide is treated successively with 180 µl (1.0 mmol) of N-ethyldiisopropylamine, 20 µl (0.3 mmol) of difluoroacetic acid, and 102 mg (0.3 mmol) of O-(benzotriazol-1-yl)-N,N,N',N'-tetramethyluronium-tetrafluoroborate (TBTU) at RT, and thereafter, stirred for 6 hours. For the working-up, the reaction mixture is evaporated under reduced pressure. The resulting residue is dissolved in 3 ml of dichloromethane and the solution is washed with 1.5 ml of a saturated solution of sodium hydrogenate and with 1.5 ml of hydrochloric acid (0.1 N). The organic phase is dried over sodium sulfate and evaporated. For purification, the crude material is chromatographed on silica gel using a 98:2-mixture of dichloromethane and methanol as the eluent. There are obtained 21 mg (18% of theory) of (S)-2,2-difluoro-N-{1-[4-(3-fluoro-benzyloxy)-phenyl]-5-oxo-pyrrolidin-3-yl}-acetamide as a white solid. MS: m/e=396 (M+NH$_4$)$^+$.

EXAMPLE 12

(S)-2,2,2-Trifluoro-N-{1-[4-(3-fluoro-benzyloxy)-phenyl]-5-oxo-pyrrolidin-3-yl}-acetamide A solution of 10 mg (0.3 mmol) of (S)-4-amino-1-[4-(3-fluoro-benzyloxy)-phenyl]-pyrrolidin-2-one hydrochloride [Example 2g)] in 2.5 ml of dichloromethane is cooled to 0° C. and treated successively with 90 µl (0.6 mmol) of triethylamine and 50 µl (0.33 mmol) of trifluoroacetic acid anhydride. The reaction mixture is left to warm to RT and stirred in total during 3.5 hours. For the working-up, the reaction mixture is diluted with 2 ml of dichloromethane. The resulting solution is washed twice with 2 ml of water, the organic layer is separated, dried over sodium sulfate, and evaporated. For purification, the crude material is chromatographed on silica gel using a 98:2-mixture of dichloromethane and methanol as the eluent. There are obtained 60 mg (51% of theory) of (S)-2,2,2-trifluoro-N-{1-[4-(3-fluoro-benzyloxy)-phenyl]-5-oxo-pyrrolidin-3-yl}-acetamide as a white solid. MS: m/e=414 (M+NH$_4$)$^+$.

EXAMPLE 13

(RS)-N-{1-[4-(4-Fluoro-benzyloxy)-phenyl]-5-oxo-pyrrolidin-3-yl}-acetamide a) (RS)-1-[4-(4-Fluoro-benzyloxy)-phenyl]-5-oxo-pyrrolidine-3-carboxylic acid methyl ester A solution of 5.0 g (21.3 mmol) of (RS)-1-(4-hydroxyphenyl)-5-oxo-pyrrolidine-3-carboxylic acid methyl ester [Example 2 b)] in 200 ml of 2-butanone is treated with 3.55 ml (27.6 mmol) of 4-fluorobenzyl-bromide and 5.88 g (42.5 mmol) of potassium carbonate and the mixture is stirred at 90° C. for 3 hours. For the working-up, the reaction mixture is diluted with ethyl acetate and extracted with water. The organic phase is separated, dried over sodium sulfate and evaporated under reduced pressure. For purification, the material obtained is chromatographed on silica gel using a 98:2-mixture dichloromethane and methanol as the eluent. There are obtained 7.18 g (98% of theory) of (RS)-1-[4-(4-fluoro-benzyloxy)-phenyl]-5-oxo-pyrrolidine-3-carboxylic acid methyl ester as a white solid. MS: m/e=344 (M+H)$^+$.

b) (RS)-1-[4-(4-Fluoro-benzyloxy)-phenyl]-5-oxo-pyrrolidine-3-carboxylic acid

A suspension of 7.12 g (20.7 mmol) of (RS)-1-[4-(4-fluoro-benzyloxy)-phenyl]-5-oxo-pyrrolidine-3-carboxylic acid methyl ester in 10.3 ml of a solution of sodium hydroxide (1N) is prepared and tetrahydrofurane is added until a clear solution is obtained. The mixture is heated to 50° C. for 1 hour. For the working-up, the tetrahydrofurane is evaporated under reduced pressure. The white suspension obtained is diluted with water, then filtered. The white product is treated with toluene and evaporated under reduced pressure to remove most of the water. The azetropic distillation is repeated three times. There are obtained 5.78 g (85% of theory) of (RS)-1-[4-(4-fluoro-benzyloxy)-phenyl]-5-oxo-pyrrolidine-3-carboxylic acid as a white solid.

c) (RS)-{1-[4-(4-Fluoro-benzyloxy)-phenyl]-5-oxo-pyrrolidin-3-yl}-carbamic acid tert-butyl ester A solution of 5.16 g (15.7 mmol) of (RS)-1-[4-(4-fluoro-benzyloxy)-phenyl]-5-oxo-pyrrolidine-3-carboxylic acid in 70 ml of tetrahydrofurane is treated with 1.76 ml (15.7 mmol) of N-methylmorpholine. Thereafter, the reaction mixture is cooled to −10° C. and 2.08 ml (15.7 mmol) of isobutyl chloroformate are added. After stirring for 3 min, a solution of 2.06 g (31.3 mmol) of sodium azide in 10 ml of water are added while the temperature rises to 0° C. After stirring for 45 min at 0° C., the suspension is diluted with 200 ml toluene and transferred into a separatory funnel. The organic layer is washed twice with 1000 ml of a saturated solution of sodium hydrogencarbonate and twice with 100 ml of a saturated solution of sodium chloride. Thereafter, the organic layer is dried over sodium sulfate and the solvent is evaporated to end with a volume of about 80 ml. The solution is heated gradually to 80° C. and kept at this temperature for 30 min. Thereafter, 35.3 ml (376 mmol) of tert-butanol are added and the mixture is stirred at 80° C. for 18 hours. Then the solvent is removed under reduced pressure, and the residue is chromatographed on silica gel using a 98:2-mixture of dichloromethane and methanol as the eluent. There are obtained 4.82 g (77% of theory) of (RS)-{1-[4-(4-fluoro-benzyloxy)-phenyl]-5-oxo-pyrrolidin-3-yl}-carbamic acid tert-butyl ester as a white solid. MS: m/e=401 (M+H)$^+$.

d) (RS)-4-Amino-1-[4-(4-fluoro-benzyloxy)-phenyl]-pyrrolidin-2-one hydrochloride In an analogous manner to that described in Example 1 f), the cleavage of the tert-butoxycarbonyl group of the (RS)-{1-[4-(4-fluoro-benzyloxy)-phenyl]-5-oxo-pyrrolidin-3-yl}-carbamic acid tert-butyl ester under acidic condition yields the (RS)-4-amino-1-[4-(4-fluoro-benzyloxy)-phenyl]-pyrrolidin-2-one hydrochloride as a white solid (yield 80% of theory). MS: m/e=301 (M+H)$^+$.

e) (RS)-N-{1-[4-(4-Fluoro-benzyloxy)-phenyl]-5-oxo-pyrrolidin-3-yl}-acetamide

In an analogous manner to that described in Example 1 g), the acetylation of (R)-4-amino-1-[4-(4-fluoro-benzyloxy)-phenyl]-pyrrolidin-2-one yields the (RS)-N-{1-[4-(4-fluoro-benzyloxy)-phenyl]-5-oxo-pyrrolidin-3-yl}-acetamide as a white solid (yield 98% of theory). MS: m/e=343 (M+H)$^+$.

EXAMPLE 14

(R)-N-{1-[4-(4-Fluoro-benzyloxy)-phenyl]-5-oxo-pyrrolidin-3-yl}-acetamide and (S)-N-{1-[4-(4-fluoro-benzyloxy)-phenyl]-5-oxo-pyrrolidin-3-yl}-acetamide The separation of 0.25 g (0.7 mmol) of the two enantiomers (RS)-N-{1-[4-(4-fluoro-benzyloxy)-phenyl]-5-oxo-pyrrolidin-3-yl}-acetamide (Example 13) is performed on a preparative chiral HPLC column (CHIRALPAK® AD, pressure: 17 bar, flow: 35 ml/min) using a 4:1 mixture of n-heptane and ethanol as the eluent. There are obtained 100 mg (39% of theory) of the first eluting (R)-(+)-N-{1-[4-(4-fluoro-benzyloxy)-phenyl]-5-oxo-pyrrolidin-3-yl}-acetamide [MS: m/e=343 (M$^+$+H)] and 90 mg (35% of theory) of the later eluting isomer (S)-(−)-N-{1-[4-(4-fluoro-benzyloxy)-phenyl]-5-oxo-pyrrolidin-3-yl}-acetamide [MS: m/e=343 (M+H)$^+$], each as a white solid.

EXAMPLE 15

(RS)-N-{1-[4-(4-Fluoro-benzyloxy)-phenyl]-5-oxo-pyrrolidin-3-yl}-formamide

In an analogous manner to that described in Example 4a), the acylation of (RS)-4-amino-1-[4-(4-fluoro-benzyloxy)-phenyl]-pyrrolidin-2-one hydrochloride [Example 13d)] yields (RS)-N-{1-[4-(4-fluoro-benzyloxy)-phenyl]-5-oxo-pyrrolidin-3-yl}-formamide as a white solid (yield 77.5% of theory). MS: m/e=328 (M+H)$^+$.

EXAMPLE 16

(RS)-N-[1-(4-Benzyloxy-phenyl)-5-oxo-pyrrolidin-3-yl]-acetamide a) (RS)-4-Amino-1-(4-benzyloxy-phenyl)-pyrrolidin-2-one hydrochloride In an analogous manner to that described in Example 1 f), the cleavage of the tert-butoxycarbonyl group of the (RS)-[1-(4-benzyloxy-phenyl)-5-oxo-pyrrolidin-3-yl]-carbamic acid tert-butyl ester [Example 1c)] yields the (RS)-4-amino-1-(4-benzyloxy-phenyl)-pyrrolidin-2-one hydrochloride as a white solid (yield 84% of theory).

b) (RS)-N-[1-(4-Benzyloxy-phenyl)-5-oxo-pyrrolidin-3-yl]-acetamide

In an analogous manner to that described in Example 1 g), the acetylation of the (RS)-4-amino-1-(4-benzyloxy-phenyl)-pyrrolidin-2-one hydrochloride yields the (RS)-N-[1-(4-benzyloxy-phenyl)-5-oxo-pyrrolidin-3-yl]-acetamide as a white solid (yield 21% of theory). MS: m/e=325 (M+H)$^+$.

EXAMPLE 17

(RS)-N-{1-[4-(2-Fluoro-benzyloxy-phenyl]-5-oxo-pyrrolidin-3-yl}-acetamide a) (RS)-1-[4-(2-Fluoro-benzyloxy)-phenyl]-5-oxo-pyrrolidine-3-carboxylic acid methyl ester In an analogous manner to that described in Example 13 a), the alkylation of the (RS)-1-(4-hydroxy-phenyl)-5-oxo-pyrrolidine-3-carboxylic acid methyl ester [Example 2 b)] with 2-fluorobenzyl-bromide using cesium carbonate as the base at RT yields (RS)-1-[4-(2-fluoro-benzyloxy)-phenyl]-5-oxo-pyrrolidine-3-carboxylic acid methyl ester as a light yellow solid (yield 82% of theory).

b) (RS)-1-[4-(2-Fluoro-benzyloxy)-phenyl]-5-oxo-pyrrolidine-3-carboxylic acid

In an analogous manner to that described in Example 13 b), the hydrolysis of the (RS)-1-[4-(2-fluoro-benzyloxy)-phenyl]-5-oxo-pyrrolidine-3-carboxylic acid methyl ester yields the (RS)-1-[4-(2-fluoro-benzyloxy)-phenyl]-5-oxo-pyrrolidine-3-carboxylic acid as an off-white solid (yield 82% of theory).

c) (RS)-4-Amino-1-[4-(2-fluoro-benzyloxy)-phenyl]-pyrrolidin-2-one hydrochloride In an analogous manner to that described in Example 2 g), the Curtius rearrangement of the (RS)-1-[4-(2-fluoro-benzyloxy)-phenyl]-5-oxo-pyrrolidine-3-carboxylic acid and the hydrolysis of the intermediate isocyanate yields the (RS)-4-amino-1-[4-(2-fluoro-benzyloxy)-phenyl]-pyrrolidin-2-one hydrochloride as a white solid (yield 85% of theory). MS: m/e=301 (M+H)$^+$.

d) (RS)-N-{1-[4-(2-Fluoro-benzyloxy)-phenyl]-5-oxo-pyrrolidin-3-yl}-acetamide

In an analogous manner to that described in Example 1 g), the acetylation of (R)-4-amino-1-[4-(2-fluoro-benzyloxy)-phenyl]-pyrrolidin-2-one yields the (RS)-N-{1-[4-(2-fluoro-benzyloxy)-phenyl]-5-oxo-pyrrolidin-3-yl}-acetamide as a white solid (yield 98% of theory). MS: m/e=343 (M+H)$^+$.

EXAMPLE 18

(RS)-(E)-N-(1-{4-[2-(3-Fluoro-phenyl)-vinyl]-phenyl}-5-oxo-pyrrolidin-3-yl)-acetamide a) (E)-1-Fluoro-3-[2-(4-nitrophenyl)ethenyl]-benzene A suspension of 677 mg of sodium hydride (55% dispersion in oil) in 10 ml of N,N-dimethylformamide is cooled to 0° C. Thereupon, 5.61 g (20.5 mmol) of diethyl (4-nitrobenzyl)phosphonate are added portionwise. The reaction mixture is left to warm to RT and stirred for 1.5 hours. Thereafter, the mixture is cooled to –10° C. and a solution of 1.5 g (12.1 mmol) of 3-fluorobenzaldehyde in 5 ml N,N-dimethylformamide is added dropwise. Stirring is continued for 30 min at 0° C., then at RT. For the working-up, ice and ethyl acetate are added to the reaction mixture. The organic layer is separated, dried over magnesium sulfate and evaporated under reduced pressure to yield the crude crystalline product, which after recrystallisation from a mixture of ether and heptane gives 2.41 g (82% of theory) of (E)-1-fluoro-3-[2-(4-nitrophenyl)ethenyl]-benzene as a yellow solid; MS: m/e=243(M)$^+$.

b) (E)-4-[2-(3-Fluoro-phenyl)-vinyl]-phenylamine

A solution of 2.41 g (10 mmol) (E)-1-fluoro-3-[2-(4-nitrophenyl)ethenyl]-benzene in 25 ml of ethyl acetate is flushed with argon and, thereafter, hydrogenated at RT and atmospheric pressure during 4 hours using 0.241 g of platinum on carbon (5%) as the catalyst. For the working-up, the catalyst is filtered over Dicalit and the resulting solution is evaporated under reduced pressure. The solid material obtained is crystallised from a mixture of ether and heptane to yield 1.32 g (62.5% of theory) of (E)-4-[2-(3-fluoro-phenyl)-vinyl]-phenylamine as an orange solid; MS: m/e=213 (M)$^+$.

c) (RS)-(E)-1-{4-[2-(3-Fluoro-phenyl)-vinyl]-phenyl}-5-oxo-pyrrolidine-3-carboxylic acid A mixture of 600 mg (2.8 mmol) of (E)-4-[2-(3-fluoro-phenyl)-vinyl]-phenylamine and 366 mg (2.8 mmol) of itaconic acid is heated to 130° C. After 1 hour, the molten material is cooled to RT and, thereafter, the resulting solid is triturated with ethyl acetate to yield 568 mg (62% of theory) of (RS)-(E)-1-{4-[2-(3-fluoro-phenyl)-vinyl]-phenyl}-5-oxo-pyrrolidine-3-carboxylic acid as a fine yellow powder; MS: m/e=324 (M–H)$^+$.

d) (RS)-(E)-(1-{4-[2-(3-Fluoro-phenyl)-vinyl]-phenyl}-5-oxo-pyrrolidin-3-yl)-carbamic acid tert-butyl ester A solution of 150 mg (0.46 mmol) of (RS)-(E)-1-{4-[2-(3-fluoro-phenyl)-vinyl]-phenyl}-5-oxo-pyrrolidine-3-carboxylic acid in 2 ml of tetrahydrofurane is cooled to –15° C. and 63 mg (0.46 mmol) of isobutyl chloroformate are added dropwise. After 5 min, a solution of 60 mg (0.92 mmol) of sodium azide in 0.5 ml water is added. The mixture is stirred at 0° C. for 45 min, then left to warm to RT. Toluene is added and the diluted solution is washed with a saturated solution of sodium hydrogencarbonate. The organic layer is separated, dried over magnesium sulfate, and evaporated under reduced pressure. The residue is dissolved in 5 ml of toluene and the solution warmed to 80° C. After 30 min, 1.1 ml (1.2 mmol) of tert-butanol are added and heating is continued for 18 hours. For the working-up, the reaction mixture is evaporated and the crude product directly chromatographed on silica gel using a 95:5-mixture of dichloromethane and methanol as the eluent. After crystallisation from ether, 104 mg (57% of theory) of (RS)-(E)- (1-{4-[2-(3-fluoro-phenyl)-vinyl]-phenyl}-5-oxo-pyrrolidin-3-yl)-carbamic acid tert-butyl ester are obtained as a light yellow solid; MS: m/e=397 (M+H)$^+$.

e) (RS)-(E)-4-Amino-1-{4-[2-(3-fluoro-phenyl)-vinyl]-phenyl}-pyrrolidin-2-one hydrochloride A solution of 104 mg (0.26 mmol) of (RS)-(E)- (1-{4-[2-(3-fluoro-phenyl)-vinyl]-phenyl}-5-oxo-pyrrolidin-3-yl)-carbamic acid tert-butyl ester in 2.5 ml of tetrahydrofurane is treated with 192 mg of hydrochloric acid (37%). The mixture is warmed to 45° C. for 2 hours, then left under stirring for 18 hours at RT. The product precipitates partially from the reaction mixture which is evaporated to yield the crude hydrochloride. This is recrystallised from ether to give 74 mg (85% of theory) of (RS)-(E)-4-amino-1-{4-[2-(3-fluoro-phenyl)-vinyl]-phenyl}-pyrrolidin-2-one hydrochloride as a white solid; MS: m/e=297 (M+H)$^+$.

f) (RS)-(E)-N-(1-{4-[2-(3-Fluoro-phenyl)-vinyl]-phenyl}-5-oxo-pyrrolidin-3-yl)-acetamide A suspension of 61 mg (0.18 mmol) of (RS)-(E)-4-amino-1-{4-[2-(3-fluoro-phenyl)-vinyl]-phenyl}-pyrrolidin-2-one hydrochloride in 2.5 ml of dichloromethane is treated with 45 mg (0.44 mmol) of triethylamine. The mixture is cooled to 0° C. and, thereafter, 20 mg (0.26 mmol) of acetylchloride are added. After 1 hour at 0° C., the mixture is left to warm to RT and is diluted with dichloromethane. After washing with water, the organic layer is dried over magnesium sulfate and evaporated. The crude product is crystallised from ether to yield 49 mg (78% of theory) of (RS)-(E)-N-(1-{4-[2-(3-fluoro-phenyl)-vinyl]-phenyl}-5-oxo-pyrrolidin-3-yl)-acetamide as a light brown solid; MS: m/e=339 (M+H)$^+$.

EXAMPLE 19

(RS)-N-(1-{4-[2-(3-Fluoro-phenyl)-ethyl]-phenyl}-5-oxo-pyrrolidin-3-yl)-acetamide a) 4-[2-(3-Fluoro-phenyl)-ethyl]-phenylamine In an analogous manner to that described in Example 18b), the hydrogenation of (E)-1-fluoro-3-[2-(4-nitrophenyl)ethenyl]-benzene [Example 18a)] using palladium on carbon (10%) during 5 hours and simultaneous reduction of the double bond yields quantitatively 4-[2-(3-fluoro-phenyl)-ethyl]-phenylamine as a yellow solid. MS: m/e=215 (M)$^+$.

b) (RS)-1-{4-[2-(3-Fluoro-phenyl)-ethyl]-phenyl}-5-oxo-pyrrolidine-3-carboxylic acid In an analogous manner to that described in Example 18c), the reaction of 4-[2-(3-fluoro-phenyl)-ethyl]-phenylamine with itaconic acid yields the (RS)-1-{4-[2-(3-fluoro-phenyl)-ethyl]-phenyl}-5-oxo-pyrrolidine-3-carboxylic acid as a light brown solid; MS: m/e=326 (M–H)$^+$.

c) (RS)-(1-{4-[2-(3-Fluoro-phenyl)-ethyl]-phenyl}-5-oxo-pyrrolidin-3-yl)-carbamic acid tert-butyl ester In an analogous manner to that described in Example 18d), the Curtius rearrangement of the (RS)-1-{4-[2-(3-fluoro-phenyl)-ethyl]-phenyl}-5-oxo-pyrrolidine-3-carboxylic acid and the treatment of the intermediate isocyanate with tert-butanol yields the (1-{4-[2-(3-fluoro-phenyl)-ethyl]-phenyl}-5-oxo-pyrrolidin-3-yl)-carbamic acid tert-butyl ester as an off-white solid (yield 36% of theory); MS: m/e=399 (M+H)$^+$.

d) (RS)-4-Amino-1-{4-[2-(3-fluoro-phenyl)-ethyl]-phenyl}-pyrrolidin-2-one hydrochloride In an analogous manner to that described in Example 18e), the cleavage of the tert-butoxycarbonyl group by hydrochlorid acid yields the (RS)-4-amino-1-{4-[2-(3-fluoro-phenyl)-ethyl]-phenyl}-pyrrolidin-2-one hydrochloride as an off-white solid (yield 67.5% of theory). MS: m/e=299 (M+H)$^+$.

e) (RS)-N-(1-{4-[2-(3-Fluoro-phenyl)-ethyl]-phenyl}-5-oxo-pyrrolidin-3-yl)-acetamide In an analogous manner to that described in Example 18f), the acetylation of the (RS)-4-amino-1-{4-[2-(3-fluoro-phenyl)-ethyl]-phenyl}-pyrrolidin-2-one yields the (RS)-N-(1-{4-[2-(3-fluoro-phenyl)-ethyl]-phenyl}-5-oxo-pyrrolidin-3-yl)-acetamide as a white solid after crystallisation in ether (yield 85.6% of theory). MS: m/e=341 (M+H)$^+$.

EXAMPLE 20

(RS)-N-{1-[6-(4-Fluoro-benzyloxy)-pyridin-3-yl]-5-oxo-pyrrolidin-3-yl}-acetamide a) 2-(4-Fluoro-benzyloxy)-5-nitro-pyridine In an analogous manner to that described in Journal of Medicinal Chemistry 33:2087–2093 (1990), the reaction of 4-fluorobenzylalcohol instead of benzylalcohol with 2-chloro-5-nitropyridine yields the 2-(4-fluoro-benzyloxy)-5-nitro-pyridine as a yellow solid.

b) 6-(4-Fluoro-benzyloxy)-pyridin-3-ylamine

A mixture of 0.70 g (2.8 mmol) of 2-(4-fluoro-benzyloxy)-5-nitro-pyridine and 2.36 g (4.2 mmol) of iron powder in 35 ml of water and 0.7 ml of acetic acid is heated under reflux for 4 hours. For the working-up, the reaction mixture is treated under vigorous stirring with water and ethyl acetate, thereafter, filtered over a layer of Dicalit. The organic layer is separated, dried over sodium sulfate and evaporated under reduced pressure. There are obtained 0.28 g (45% of theory) of 6-(4-fluoro-benzyloxy)-pyridin-3-ylamine as a greenish solid which is engaged in the next step without further purification.

c) (RS)-1-[6-(4-Fluoro-benzyloxy)-pyridin-3-yl]-5-oxo-pyrrolidine-3-carboxylic acid In an analogous manner to that described in Example 1a), the reaction of 6-(4-fluoro-benzyloxy)-pyridin-3-ylamine with itaconic acid yields (RS)-1-[6-(4-fluoro-benzyloxy)-pyridin-3-yl]-5-oxo-pyrrolidine-3-carboxylic acid as a green solid (yield 47% of theory).

d) (RS)-4-Amino-1-[6-(4-fluoro-benzyloxy)-pyridin-3-yl]-pyrrolidin-2-one dihydrochloride In an analogous manner to that described in Example 2 g), the Curtius rearrangement of (RS)-1-[6-(4-fluoro-benzyloxy)-pyridin-3-yl]-5-oxo-pyrrolidine-3-carboxylic acid and treatment of the intermediate isocyanate yields (RS)-4-amino-1-[6-(4-fluoro-benzyloxy)-pyridin-3-yl]-pyrrolidin-2-one dihydrochloride as a light yellow solid.

e) (RS)-N-{1-[6-(4-Fluoro-benzyloxy)-pyridin-3-yl]-5-oxo-pyrrolidin-3-yl}-acetamide In an analogous manner to that described in Example 1 g), the acetylation of (RS)-4-amino-1-[6-(4-fluoro-benzyloxy)-pyridin-3-yl]-pyrrolidin-2-one dihydrochloride yields (RS)-N-{1-[6-(4-fluoro-benzyloxy)-pyridin-3-yl]-5-oxo-pyrrolidin-3-yl}-acetamide as a white solid (yield 37% of theory). MS: m/e=344 (M+H)$^+$.

EXAMPLE 21

(S)-N-{1-[4-(3–Chloro-benzyloxy)-phenyl]-5-oxo-pyrrolidin-3-yl}-acetamide a) (S)-N-[1-(4-Hydroxy-phenyl)-5-oxo-pyrrolidin-3-yl]-acetamide A solution of 4.67 g (13.6 mmol) of (S)-N-{1-[4-(3-fluoro-benzyloxy)-phenyl]-5-oxo-pyrrolidin-3-yl}-acetamide in 500 ml of tetrahydrofurane is hydrogenated in the presence of 726 mg palladium on carbon (10%) at ambient pressure and RT during 18 hours. The reaction not being complete, the catalyst is filtered over Dicalit and another 726 mg of palladium on carbon (10%) are added. For the working-up, the reaction mixture is filtered over Dicalit, then evaporated under reduced pressure. The crude (S)-N-[1-(4-hydroxy-phenyl)-5-oxo-pyrrolidin-3-yl]-acetamide is obtained as an off-white solid, which is directly engaged in the next step without further purification. MS: m/e=235 (M+H)$^+$ b) (S)-N-{1-[4-(3–Chloro-benzyloxy)-phenyl]-5-oxo-pyrrolidin-3-yl}-acetamide A solution of 15 mg (0.064 mmol) of (S)-N-[1-(4-hydroxy-phenyl)-5-oxo-pyrrolidin-3-yl]-acetamide in 30 ml of acetone is treated with 0.01 ml (0.074 mmol) of 2-chlorobenzyl-bromide and 22 mg (0.067 mmol) of cesium carbonate and the mixture is stirred at 40° C. for 4 hours. For the working-up, the reaction mixture is filtrated and evaporated to dryness. The residue is chromatographed on silica gel using a 19:1 mixture dichloromethane and methanol as the eluent. There are obtained 17 mg (72% of theory) of (S)-N-{1-[4-(3-chloro-benzyloxy)-phenyl]-5-oxo-pyrrolidin-3-yl}-acetamide as a white solid. MS: m/e=359.3 (M+H)$^+$.

EXAMPLE 22

(S)-N-{1-[4-(2,6-Difluoro-benzyloxy)-phenyl]-5-oxo-pyrrolidin-3-yl} acetamide

In an analogous manner to that described in Example 21b), starting from (S)-N-[1-(4-hydroxy-phenyl)-5-oxo-pyrrolidin-3-yl]-acetamide [example 21a] the title compound is prepared by alkylation with 2,6-difluorobenzyl bromide and cesium carbonate at 40° C. overnight. Yield 85% of theory as a white solid. MS: m/e=361.3 (M+H)$^+$.

EXAMPLE 23

(S)-N-{5-Oxo-1-[4-(2,4,6-trifluoro-benzyloxy)-phenyl]-pyrrolidin-3-yl}-acetamide In an analogous manner to that described in Example 21b), starting from (S)-N-[1-(4-Hydroxy-phenyl)-5-oxo-pyrrolidin-3-yl]-acetamide [example 21a] the title compound is prepared by alkylation with 2,4,6-trifluorobenzyl bromide and cesium carbonate at 40° C. overnight. Yield 53% of theory as a white solid. MS: m/e=379.4 (M+H)$^+$.

EXAMPLE 24

(S)-N-{1-[4-(3-Methoxy-benzyloxy)-phenyl]-5-oxo-pyrrolidin-3-yl}-acetamide

In an analogous manner to that described in Example 21b), starting from (S)-N-[1-(4-hydroxy-phenyl)-5-oxo-pyrrolidin-3-yl]-acetamide [example 21a] the title compound is prepared by alkylation with 3-methoxybenzyl bromide and cesium carbonate at 40° C. overnight. Yield 58% of theory as a white solid. MS: m/e=355.2 (M+H)$^+$.

EXAMPLE 25

(S)-N-{5-Oxo-1-[4-(4-trifluoromethyl-benzyloxy)-phenyl]-pyrrolidin-3-yl}-acetamide In an analogous manner to that described in Example 21b), starting from (S)-N-[1-(4-hydroxy-phenyl)-5-oxo-pyrrolidin-3-yl]-acetamide [example 21a] the title compound is prepared by alkylation with 4-(trifluoromethyl)benzyl bromide and cesium carbonate at 40° C. overnight. Yield 55% of theory as a white solid. MS: m/e=393.3(M+H)$^+$.

EXAMPLE 26

(S)-N-{1-[4-(4-Methyl-benzyloxy)-phenyl]-5-oxo-pyrrolidin-3-yl}-acetamide

In an analogous manner to that described in Example 21b), starting from (S)-N-[1-(4-hydroxy-phenyl)-5-oxo-pyrrolidin-3-yl]-acetamide [example 21a] the title compound is prepared by alkylation with 4-methylbenzyl bromide and cesium carbonate at 40° C. overnight. Yield 83% of theory as a white solid. MS: m/e=339.1 (M+H)$^+$.

EXAMPLE 27

(S)-N-{1-[4-(3–Cyano-benzyloxy)-phenyl]-5-oxo-pyrrolidin-3-yl}-acetamide

In an analogous manner to that described in Example 21b), starting from (S)-N-[1-(4-hydroxy-phenyl)-5-oxo-pyrrolidin-3-yl]-acetamide [example 21a] the title compound is prepared by alkylation with 3-(bromomethyl)benzonitrile and cesium carbonate at 40° C. overnight. Yield 91% of theory as a light yellow solid. MS: m/e=350.3(M+H)$^+$.

The following Examples A to D are prophetic.

EXAMPLE A

Tablets

Tablets of the following composition are produced in a conventional manner:

|  | mg/Tablet |
| --- | --- |
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets

Tablets of the following composition are produced in a conventional manner:

|  | mg/Tablet |
| --- | --- |
| Active ingredient | 200 |
| Powdered lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules

Capsules of the following composition are produced:

|  | mg/Capsule |
| --- | --- |
| Active ingredient | 50 |
| Crystalline lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

EXAMPLE D

Injection Solution

An injection solution may have the following composition and is manufactured in usual manner:

| Active substance | 1.0 mg |
| --- | --- |
| 1 N HCl | 20.0 µl |
| acetic acid | 0.5 mg |
| NaCl | 8.0 mg |
| phenol | 10.0 mg |

| | |
|---|---|
| 1 N NaOH | q.s. ad pH 5 |
| H₂O | q.s. ad 1 ml |

The invention claimed is:

1. A compound of the formula I

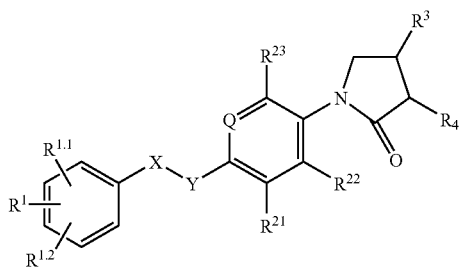

wherein
Q is =N— or =C(R²⁴)—;
X—Y is —CH₂—CH₂—, —CH=CH— or —CH₂—O—;
R¹, R¹·¹ and R¹·² independently from each other are selected from the group consisting of hydrogen, halogen, halogen-(C₁–C₆)-alkyl, cyano, (C₁–C₆)-alkoxy or halogen-(C₁–C₆)-alkoxy;
R²¹ R²² and R²³ independently from each other are selected from the group consisting of hydrogen and halogen;
R²⁴ is hydrogen, halogen or methyl;
R³ is —NHR⁶;
R⁴ is hydrogen; and
R⁶ is —C(O)H, —C(O)—(C₁–C₃)-alkyl, C(O)-halogen-(C₁–C₃)alkyl, —C(O)O(C₁–C₃)-alkyl, —C(O)NH₂ or —SO₂—(C₁–C₃)-alkyl;
or an individual isomer or racemic or non-racemic mixture thereof.

2. A compound of claim 1 wherein Q is =C(R²⁴)—.

3. A compound of claim 2 wherein R²⁴ is hydrogen; X—Y is —CH₂—O—; R¹·¹ and R¹·² are hydrogen; R¹ is hydrogen or halogen; R²¹, R²², and R²³ are hydrogen; R⁴ is hydrogen, and R³ is NHR⁶.

4. A compound of claim 3 wherein R⁶ is COOH, C(O)CH₃, C(O)CH₂F, C(O)CHF₂, C(O)CF₃, C(O)OCH₃, C(O)NH₂, or SO₂CH₃.

5. A compound of claim 1 wherein Q is =CH—, =CF—, or =C(CH₃)—.

6. A compound of claim 1 wherein Q is =N—.

7. A compound of claim 1 wherein X—Y is —CH₂—O—.

8. A compound of claim 1 wherein X—Y is —CH₂—CH₂— or —CH=CH—.

9. A compound of claim 1 wherein R¹, R¹·¹, and R¹·² independently are selected from the group consisting of hydrogen, halogen, cyano, methyl, halogenmethyl, methoxy or halogenmethoxy.

10. A compound of claim 1 wherein R¹, R¹·¹, and R¹·² are halogen.

11. A compound of claim 10 wherein R¹, R¹·¹, and R¹·² are fluoro.

12. A compound of claim 11 wherein R¹, R¹·¹, and R¹·² are 2,4,6-trifluoro, 2,4,5-trifluoro, 2,3,6-trifluoro, 2,3,4-trifluoro, or 3,4,5-trifluoro.

13. A compound of claim 1 wherein R¹·² is hydrogen and R¹ and R¹·¹ independently from each other are selected from the group consisting of hydrogen, halogen, cyano, (C₁–C₆)-alkyl, halogen-(C₁–C₆)-alkyl, (C₁–C₆)-alkoxy or halogen-(C₁–C₆)-alkoxy.

14. A compound of claim 13 wherein R¹ and R¹·¹ independently are halogen or (C₁–C₆)-alkyl.

15. A compound of claim 14 wherein R¹·¹ is halogen and R¹ is halogen or (C₁–C₆)-alkyl.

16. A compound of claim 1 wherein R¹, R¹·¹ and R¹·² are hydrogen.

17. A compound of claim 1 wherein R¹·¹ and R¹·² are hydrogen and R¹ is selected from the group consisting of hydrogen, halogen, cyano, (C₁–C₆)-alkyl, halogen-(C₁–C₆)-alkyl, (C₁–C₆)-alkoxy or halogen-(C₁–C₆)-alkoxy.

18. A compound of claim 17 wherein R¹ is halogen or (C₁–C₆)-alkyl.

19. A compound of claim 17 wherein R¹ is selected from the group consisting of hydrogen, halogen, cyano, methyl, halogenmethyl, methoxy or halogenmethoxy.

20. A compound of claim 19 wherein R¹ is halogenmethoxy.

21. A compound of claim 20 wherein R¹ is 3-trifluoromethoxy.

22. A compound of claim 19 wherein R¹ is fluoro.

23. A compound of claim 22 wherein R¹ is 3-fluoro or 4-fluoro.

24. A compound of claim 19 wherein R¹ is methyl.

25. A compound of claim 24 wherein R¹ is 4-methyl.

26. A compound of claim 19 wherein R¹ is chloro.

27. A compound of claim 26 wherein R¹ is 3-chloro.

28. A compound of claim 19 wherein R¹ is CN.

29. A compound of claim 19 wherein R¹ is halogenmethyl.

30. A compound of claim 29 wherein R¹ is 3-trifluoromethyl.

31. A compound of claim 19 wherein R¹ is methoxy.

32. A compound of claim 31 wherein R¹ is 2-methoxy, 3-methoxy, or 4-methoxy.

33. A compound of claim 1 wherein R²¹, R²² and R²³ are hydrogen.

34. A compound of claim 1 wherein R²⁴ is hydrogen.

35. A compound of claim 1 wherein R³ is —NHR⁶ wherein R⁶ is —C(O)H, —C(O)—CH₃, —C(O)—CH₂F, —C(O)—CHF₂, —C(O)—CF₃, —C(O)O—CH₃, —C(O)—NH₂ or —SO₂—CH₃.

36. A compound of claim 1 wherein the compound has (S)-configuration.

37. A compound of the formula I*

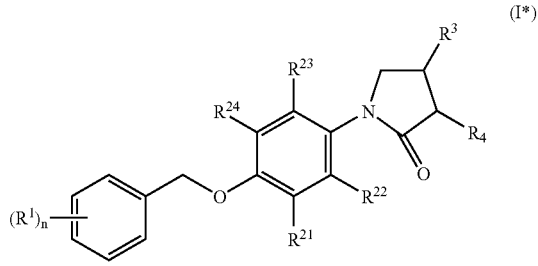

wherein
R¹ is halogen, halogen-(C₁–C₆)-alkyl, cyano, (C₁–C₆)-alkoxy or halogen-(C₁–C₆)-alkyl;

R²¹, R²², R²³ and R²⁴ independently from each other are selected from the group consisting of hydrogen and halogen;
R³ is —NHR⁶;
R⁴ is hydrogen;
R⁶ is —CO—(C₁–C₃)-alkyl or —SO₂—(C₁–C₃)-alkyl; and
n is 0, 1, 2 or 3;
or an individual isomer or a racemic or non-racemic mixture thereof.

38. A compound of claim 37 wherein R³ is NHR⁶; R⁶ is —CO—(C₁–C₆)-alkyl or —SO₂—(C₁–C₆)-alkyl; and R⁴ is hydrogen.

39. A compound of claim 37 wherein n is 1 or 2.

40. A compound of claim 37 wherein n is 0 or 1.

41. A compound of claim 37 wherein n is 1.

42. A compound of claim 37 wherein R¹ is halogen or halogen-(C₁–C₆)-alkyl.

43. A compound of claim 42 wherein R¹ is fluoro, chloro, or trifluoromethyl.

44. A compound selected from the group consisting of
(RS)-N-{1-[4-(3-fluoro-benzyloxy)-phenyl]-5-oxo-pyrrolidin-3-yl}-acetamide,
(S)-N-{1-[4-(3-fluoro-benzyloxy)-phenyl]-5-oxo-pyrrolidin-3-yl}-acetamide,
(R)-N-{1-[4-(3-fluoro-benzyloxy)-phenyl]-5-oxo-pyrrolidin-3-yl}-acetamide,
(RS)-N-{1-[4-(3-fluoro-benzyloxy)-phenyl]-5-oxo-pyrrolidin-3-yl}-formamide,
(S)-N-{1-[4-(3-fluoro-benzyloxy)-phenyl]-5-oxo-pyrrolidin-3-yl}-formamide,
(R)-N-{1-[4-(3-fluoro-benzyloxy)-phenyl]-5-oxo-pyrrolidin-3-yl}-formamide,
(RS)-{1-[4-(3-fluoro-benzyloxy)-phenyl]-5-oxo-pyrrolidin-3-yl}-carbamic acid methyl ester,
(RS)-{1-[4-(3-fluoro-benzyloxy)-phenyl]-5-oxo-pyrrolidin-3-yl}-urea, and
(RS)-N-{1-[4-(3-fluoro-benzyloxy)-phenyl]-5-oxo-pyrrolidin-3-yl}-methanesulfonamide.

45. A compound selected from the group consisting of
(S)-2-fluoro-N-{1-[4-(3-fluoro-benzyloxy)-phenyl]-5-oxo-pyrrolidin-3-yl}-acetamide,
(S)-2,2-difluoro-N-{1-[4-(3-fluoro-benzyloxy)-phenyl]-5-oxo-pyrrolidin-3-yl}-acetamide,
(S)-2,2,2-trifluoro-N-{1-[4-(3-fluoro-benzyloxy)-phenyl]-5-oxo-pyrrolidin-3-yl}-acetamide,
(RS)-N-{1-[4-(4-fluoro-benzyloxy)-phenyl]-5-oxo-pyrrolidin-3-yl}-acetamide,
(R)-N-{1-[4-(4-fluoro-benzyloxy)-phenyl]-5-oxo-pyrrolidin-3-yl}-acetamide,
(S)-N-{1-[4-(4-fluoro-benzyloxy)-phenyl]-5-oxo-pyrrolidin-3-yl}-acetamide,
(RS)-N-{1-[4-(4-fluoro-benzyloxy)-phenyl]-5-oxo-pyrrolidin-3-yl}-formamide,
(RS)-N-[1-(4-benzyloxy-phenyl)-5-oxo-pyrrolidin-3-yl]-acetamide, and
(RS)-N-{1-[4-(2-fluoro-benzyloxy-phenyl]-5-oxo-pyrrolidin-3-yl}-acetamide.

46. A compound selected from the group consisting of
(RS)-(E)-N-(1-{4-[2-(3-fluoro-phenyl)-vinyl]-phenyl}-5-oxo-pyrrolidin-3-yl)-acetamide,
(RS)-N-(1-{4-[2-(3-fluoro-phenyl)-ethyl]-phenyl}-5-oxo-pyrrolidin-3-yl)-acetamide,
(RS)-N-{1-[6-(4-fluoro-benzyloxy)-pyridin-3-yl]-5-oxo-pyrrolidin-3-yl}-acetamide,
(S)-N-{1-[4-(3-chloro-benzyloxy)-phenyl]-5-oxo-pyrrolidin-3-yl}-acetamide,
(S)-N-{1-[4-(2,6-difluoro-benzyloxy)-phenyl]-5-oxo-pyrrolidin-3-yl} acetamide,
(S)-N-{5-oxo-1-[4-(2,4,6-trifluoro-benzyloxy)-phenyl]-pyrrolidin-3-yl}-acetamide,
(S)-N-{1-[4-(3-methoxy-benzyloxy)-phenyl]-5-oxo-pyrrolidin-3-yl}-acetamide,
(S)-N-{5-oxo-1-[4-(4-trifluoromethyl-benzyloxy)-phenyl]-pyrrolidin-3-yl}-acetamide,
(S)-N-{1-[4-(4-methyl-benzyloxy)-phenyl]-5-oxo-pyrrolidin-3-yl}-acetamide, and
(S)-N-{1-[4-(3-cyano-benzyloxy)-phenyl]-5-oxo-pyrrolidin-3-yl}-acetamide.

47. A composition comprising a compound of formula I

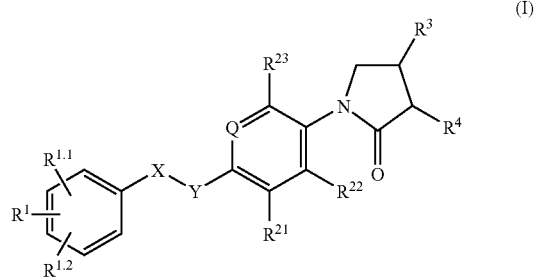

(I)

wherein
Q is =N— or =C(R²⁴)—;
X—Y is —CH₂—CH₂—, —CH=CH— or —CH₂—O—;
R¹, R¹·¹ and R¹·² independently from each other are selected from the group consisting of hydrogen, halogen, halogen-(C₁–C₆)-alkyl, cyano, (C₁–C₆)-alkoxy or halogen-(C₁–C₆)-alkoxy;
R²¹, R²² and R²³ independently from each other are selected from the group consisting of hydrogen and halogen;
R²⁴ is hydrogen, halogen or methyl;
R³ is —NHR⁶;
R⁴ is hydrogen; and
R⁶ is —C(O)H, —C(O)—(C₁–C₃)-alkyl, C(O)-halogen-(C₁–C₃)alkyl, —C(O)O(C₁–C₃)-alkyl, —C(O)NH₂ or —SO₂—(C₁–C₃)-alkyl;
or an individual isomer or racemic or non-racemic mixture thereof, and a pharmaceutically acceptable carrier.

48. A composition comprising a compound of formula I*

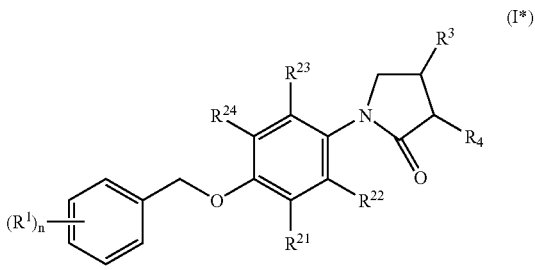

(I*)

wherein
R¹ is halogen, halogen-(C₁–C₆)-alkyl, cyano, (C₁–C₆)-alkoxy or halogen-(C₁–C₆)-alkoxy;
R²¹, R²², R²³ and R²⁴ independently from each other are selected from the group consisting of hydrogen and halogen;

$R^3$ is —$NHR^6$;
$R^4$ is hydrogen;
$R^6$ is —CO—($C_1$–$C_3$)-alkyl or —$SO_2$—($C_1$–$C_3$)-alkyl; and
n is 0, 1, 2 or 3;
or an individual isomer or racemic or non-racemic mixture thereof, and a pharmaceutically acceptable carrier.

49. A process for the preparation of compounds of formula I according to claim 1 comprising reacting a compound of formula II

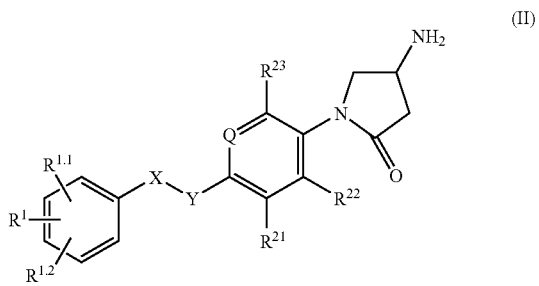

with an isocyanate or an acyl donating agent of formula Z-C(O)—($C_1$–$C_3$)-alkyl, Z-C(O)-halogen-($C_1$–$C_3$)alkyl, Z-C(O)O($C_1$–$C_3$)-alkyl, or Z-$SO_2$—($C_1$–$C_3$)-alkyl wherein Z is an activating group.

50. A method for the treatment of Alzheimer's disease comprising administering to an individual a therapeutically effective amount of a compound of claim 1.

51. A method for the treatment of senile dementia comprising administering to an individual a therapeutically effective amount of a compound of claim 1.

* * * * *